(12) United States Patent
Lira et al.

(10) Patent No.: US 8,304,604 B2
(45) Date of Patent: Nov. 6, 2012

(54) DIG-3 INSECTICIDAL CRY TOXINS

(75) Inventors: Justin M. Lira, Fishers, IN (US); Holly J. Butler, Indianapolis, IN (US); Doug A. Smith, Noblesville, IN (US); Kenneth Narva, Zionsville, IN (US); Thomas Meade, Zionsville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 293 days.

(21) Appl. No.: 12/730,295

(22) Filed: Mar. 24, 2010

(65) Prior Publication Data

US 2010/0269223 A1    Oct. 21, 2010

Related U.S. Application Data

(60) Provisional application No. 61/170,189, filed on Apr. 17, 2009.

(51) Int. Cl.
*A01H 5/00* (2006.01)
*A01N 57/18* (2006.01)
*C12N 15/63* (2006.01)
*C12N 15/82* (2006.01)
*C12N 15/32* (2006.01)
*C07K 14/325* (2006.01)

(52) U.S. Cl. ......... 800/279; 800/302; 530/350; 514/4.5; 536/23.71; 435/418; 435/320.1

(58) Field of Classification Search .................. None
See application file for complete search history.

(56) References Cited

U.S. PATENT DOCUMENTS

2009/0313722 A1 *  12/2009  Abad et al. ................... 800/279

OTHER PUBLICATIONS de Maagd et al (Trends in Genetics, 2001, 17(4), 193-199).*
Soberón et al ("Sciencexpress" (2007) p. 1-7).*
Nunez-Valez et al (Biochemica et Biophyscia Acta (2001) 122-131).*
Isakova et al (Uniprot Acession No. Q8KNY2, first available online Oct. 1, 2002).*

* cited by examiner

*Primary Examiner* — Anne Grunberg
*Assistant Examiner* — Lee A Visone
(74) *Attorney, Agent, or Firm* — Ronald S. Maciak; Faegre Baker Daniels, LLP.

(57) ABSTRACT

DIG-3 Cry toxins, polynucleotides encoding such toxins, and transgenic plants that produce such toxins are useful to control insect pests.

12 Claims, No Drawings

DIG-3 INSECTICIDAL CRY TOXINS

CROSS REFERENCE TO RELATED APPLICATIONS

This application claims benefit to U.S. Provisional Patent Application No. 61/170,189, filed Apr. 17, 2009, which is expressly incorporated by reference herein.

FIELD OF THE INVENTION

This invention concerns new insecticidal Cry toxins and their use to control insects.

BACKGROUND OF THE INVENTION

*Bacillus thuringiensis* (B.t.) is a soil-borne bacterium that produces pesticidal crystal proteins known as delta endotoxins or Cry proteins. Cry proteins are oral intoxicants that function by acting on midgut cells of susceptible insects. An extensive list of delta endotoxins is maintained and regularly updated at http://www.lifesci.sussex.ac.uk/home/Neil_Crickmore/Bt/intro.html.

European corn borer (ECB), *Ostrinia nubilalis* (Hübner), is the most damaging insect pest of corn throughout the United States and Canada, and causes an estimated $1 billion revenue loss each year due to crop yield loss and expenditures for insect management (Witkowski et al., 2002). Transgenic corn expressing genes encoding Cry proteins, most notably Cry1Ab, Cry1Ac, or Cry1F, provide commercial levels of efficacy against ECB.

Despite the success of ECB-resistant transgenic corn, the possibility of the development of resistant insect populations threatens the long-term durability of Cry proteins in ECB control and creates the need to discover and develop new Cry proteins to control ECB and other pests. Insect resistance to B.t. Cry proteins can develop through several mechanisms (Heckel et al., 2007, Pigott and Ellar, 2007). Multiple receptor protein classes for Cry proteins have been identified within insects, and multiple examples exist within each receptor class. Resistance to a particular Cry protein may develop, for example, by means of a mutation within the toxin-binding portion of a cadherin domain of a receptor protein. A further means of resistance may be mediated through a protoxin-processing protease. Thus, resistance to Cry toxins in species of *Lepidoptera* has a complex genetic basis, with at least four distinct, major resistance genes. Lepidopteran insects resistant to Cry proteins have developed in the field within the species *Plutella xylostella* (Tabashnik, 1994), *Trichoplusia ni* (Janmaat and Myers 2003, 2005), and *Helicoverpa zeae* (Tabashnik et al., 2008). Development of new high potency Cry proteins would provide additional tools for management of ECB and other insect pests. Cry proteins with different modes of action produced in combination in transgenic corn would prevent the development ECB insect resistance and protect the long term utility of B.t. technology for insect pest control.

BRIEF SUMMARY OF THE INVENTION

The present invention provides insecticidal Cry toxins, including the toxin designated herein as DIG-3 as well as variants of DIG-3, nucleic acids encoding these toxins, methods of controlling pests using the toxins, methods of producing the toxins in transgenic host cells, and transgenic plants that produce the toxins. The predicted amino acid sequence of the wild type DIG-3 toxin is given in SEQ ID NO:2.

As described in Example 1, a nucleic acid encoding the DIG-3 protein was isolated from a B.t. strain internally designated by Dow AgroSciences LLC as PS46L. The nucleic acid sequence for the full length coding region was determined, and the full length protein sequence was deduced from the nucleic acid sequence. The DIG-3 toxin has some similarity to Cry1BII (Genbank Accession No. AAM93496) and other *B. thuringiensis* Cry1B-type proteins (http://www.lifesci.sussex.ac.uk/home/Neil_Crickmore/Bt/intro.html).

Insecticidally active variants of the DIG-3 toxin are also described herein, and are referred to collectively as DIG-3 toxins.

DIG-3 toxins may also be used in combination with RNAi methodologies for control of other insect pests. For example, DIG-3 can be used in transgenic plants in combination with a dsRNA for suppression of an essential gene in corn rootworm or an essential gene in an insect pest. Such target genes include, for example, vacuolar ATPase, ARF-1, Act42A, CHD3, EF-1α, and TFIIB. An example of a suitable target gene is vacuolar ATPase, as disclosed in WO2007/035650.

A surprising finding reported herein is that DIG-3 toxins are active against populations of European corn borer and diamond back moth that are resistant to Cry1F and Cry1A toxins. Accordingly, DIG-3 toxins are ideal candidates for use to control of Lepidopteran pests. The toxins can be used alone or in combination with other Cry toxins, such as Cry1F, Cry1Ab, and Cry1Ac, to control development of resistant insect populations.

Insecticidally active fragments of SEQ ID NO:2, and nucleotides encoding such fragments, are another aspect of the invention.

In one embodiment the invention provides an isolated DIG-3 toxin polypeptide comprising a core toxin segment selected from the group consisting of
  (a) a polypeptide comprising the amino acid sequence of residues 113 to 643 of SEQ ID NO:2;
  (b) a polypeptide comprising an amino acid sequence having at least 90% sequence identity to the amino acid sequence of residues 113 to 643 of SEQ ID NO:2;
  (c) a polypeptide comprising an amino acid sequence of residues 113 to 643 of SEQ ID NO:2 with up to 20 amino acid substitutions, deletions, or modifications that do not adversely affect expression or activity of the toxin encoded by SEQ ID NO:2.

In one embodiment the invention provides an isolated DIG-3 toxin polypeptide comprising a core toxin segment selected from the group consisting of
  (a) a polypeptide comprising the amino acid sequence of residues 73 to 643 of SEQ ID NO:2;
  (b) a polypeptide comprising an amino acid sequence having at least 90% sequence identity to the amino acid sequence of residues 73 to 643 of SEQ ID NO:2;
  (c) a polypeptide comprising an amino acid sequence of residues 73 to 643 of SEQ ID NO:2 with up to 20 amino acid substitutions, deletions, or modifications that do not adversely affect expression or activity of the toxin encoded by SEQ ID NO:2.

In another embodiment the invention provides an isolated DIG-3 toxin polypeptide comprising a DIG-3 core toxin segment selected from the group consisting of
  (a) a polypeptide comprising the amino acid sequence of residues 1 to 643 of SEQ ID NO:2;
  (b) a polypeptide comprising an amino acid sequence having at least 90% sequence identity to the amino acid sequence of residues 1 to 643 of SEQ ID NO:2;
  (c) a polypeptide comprising an amino acid sequence of residues 1 to 643 of SEQ ID NO:2 with up to 20 amino acid substitutions, deletions, or modifications that do not adversely affect expression or activity of the toxin encoded by SEQ ID NO:2.

By "isolated" applicants mean that the polypeptide or DNA molecules have been removed from their native environment and have been placed in a different environment by the hand of man.

In another embodiment the invention provides a plant comprising a DIG-3 toxin.

In another embodiment the invention provides a method for controlling a pest population comprising contacting said population with a pesticidally effective amount of a DIG-3 toxin.

In another embodiment the invention provides an isolated nucleic acid that encodes a DIG-3 toxin.

In another embodiment the invention provides a DNA construct comprising a nucleotide sequence that encodes a DIG-3 toxin operably linked to a promoter that is not derived from *Bacillus thuringiensis* and is capable of driving expression in a plant. The invention also provides a transgenic plant that comprises the DNA construct stably incorporated into its genome and a method for protecting a plant from a pest comprising introducing the construct into said plant.

BRIEF DESCRIPTION OF THE SEQUENCES

SEQ ID NO:1 DNA sequence encoding full-length DIG-3 toxin; 3771 nt.
SEQ ID NO:2 Full-length DIG-3 protein sequence; 1256 aa.
SEQ ID NO:3 Plant-optimized full length DIG-3 DNA sequence; 3771 nt.
SEQ ID NO:4 Cry1Ab protoxin segment; 545 aa.
SEQ ID NO:5 Chimeric toxin: DIG-3 Core toxin segment/Cry1Ab protoxin segment; 1188 aa.
SEQ ID NO:6 Dicot-optimized DNA sequence encoding the Cry1Ab protoxin segment; 1635 nt
SEQ ID NO:7 Maize-optimized DNA sequence encoding the Cry1Ab protoxin segment; 1635 nt

DETAILED DESCRIPTION OF THE INVENTION

DIG-3 Toxins, and insecticidally active variants. In addition to the full length DIG-3 toxin of SEQ ID NO:2, the invention encompasses insecticidally active variants. By the term "variant", applicants intend to include fragments, certain deletion and insertion mutants, and certain fusion proteins. DIG-3 is a classic three-domain Cry toxin. As a preface to describing variants of the DIG-3 toxin that are included in the invention, it will be useful to briefly review the architecture of three-domain Cry toxins in general and of the DIG-3 protein toxin in particular.

A majority of *Bacillus thuringiensis* delta-endotoxin crystal protein molecules are composed of two functional segments. The protease-resistant core toxin is the first segment and corresponds to about the first half of the protein molecule. The full ~130 kDa protoxin molecule is rapidly processed to the resistant core segment by proteases in the insect gut. The segment that is deleted by this processing will be referred to herein as the "protoxin segment". The protoxin segment is believed to participate in toxin crystal formation (Arvidson et al., 1989). The protoxin segment may thus convey a partial insect specificity for the toxin by limiting the accessibility of the core to the insect by reducing the protease processing of the toxin molecule (Haider et al., 1986) or by reducing toxin solubility (Aronson et al., 1991). B.t. toxins, even within a certain class, vary to some extent in length and in the precise location of the transition from the core toxin segment to protoxin segment. The transition from core toxin segment to protoxin segment will typically occur at between about 50% to about 60% of the full length toxin. SEQ ID NO:2 discloses the 1256 amino acid sequence of the full-length DIG-3 polypeptide, of which the N-terminal 643 amino acids comprise the DIG-3 core toxin segment. The 5'-terminal 1929 nucleotides of SEQ ID NO:1 comprise the coding region for the core toxin segment.

Three dimensional crystal structures have been determined for Cry1Aa1, Cry2Aa1, Cry3Aa1, Cry3Bb1, Cry4Aa, Cry4Ba and Cry8Ea1. These structures for the core toxins are remarkably similar and are comprised of three distinct domains with the features described below (reviewed in de Maagd et al., 2003).

Domain I is a bundle of seven alpha helices where α-helix 5 is surrounded by six amphipathic helices. This domain has been implicated in pore formation and shares homology with other pore forming proteins including hemolysins and colicins. Domain I of the DIG-3 protein comprises amino acid residues 56 to 278 of SEQ ID NO:2.

Domain II is formed by three anti-parallel beta sheets packed together in a beta prism. The loops of this domain play important roles in binding insect midgut receptors. In Cry1A proteins, surface exposed loops at the apices of Domain II beta sheets are involved in binding to Lepidopteran cadherin receptors. Cry3Aa Domain II loops bind a membrane-associated metalloprotease of *Leptinotarsa decemlineata* (Say) (Colorado potato beetle) in a similar fashion (Ochoa-Campuzano et al., 2007). Domain II shares homology with certain carbohydrate-binding proteins including vitelline and jacaline. Domain II of the DIG-3 protein comprises amino acid residues 283 to 493 of SEQ ID NO:2.

Domain III is a beta sandwich of two anti-parallel beta sheets. Structurally this domain is related to carbohydrate-binding domains of proteins such as glucanases, galactose oxidase, sialidase and others. Domain III binds certain classes of receptor proteins and perhaps participates in insertion of an oligomeric toxin pre-pore that interacts with a second class of receptors, examples of which are aminopeptidase and alkaline phosphatase in the case of Cry1A proteins (Pigott and Ellar, 2007). Analogous Cry Domain III receptors have yet to be identified in Coleoptera. Conserved B.t. sequence blocks 2 and 3 map near the N-terminus and C-terminus of Domain 2, respectively. Hence, these conserved sequence blocks 2 and 3 are approximate boundary regions between the three functional domains. These regions of conserved DNA and protein homology have been exploited for engineering recombinant B.t. toxins (U.S. Pat. No. 6,090,931, WO 91/01087, WO 95/06730, WO 1998022595). Domain III of the DIG-3 protein comprises amino acid residues 503 to 641 of SEQ ID NO:2.

It has been reported that α-helix 1 of Domain I is removed following receptor binding. Aronson et al. (1999) demonstrated that Cry1Ac bound to BBMV was protected from proteinase K cleavage beginning at residue 59, just after α-helix 1; similar results were cited for Cry1Ab. Gomez et al. (2002) found that Cry1Ab oligomers formed upon BBMV receptor binding lacked the α-helix 1 portion of Domain I. Also, Soberon et al. (2007) have shown that N-terminal deletion mutants of Cry1Ab and Cry1Ac which lack approximately 60 amino acids encompassing α-helix 1 on the three dimensional Cry structure are capable of assembling monomers of molecular weight about 60 kDa into pre-pores in the absence of cadherin binding. These N-terminal deletion mutants were reported to be active on Cry-resistant insect larvae. Furthermore, Diaz-Mendoza et al. (2007) described Cry1Ab fragments of 43 kDa and 46 kDa that retained activity on Mediterranean corn borer (*Sesamia nonagrioides*). These fragments were demonstrated to include amino acid residues 116 to 423; however the precise amino acid sequences were not elucidated and the mechanism of activity of these proteolytic fragments is unknown. The results of Gomez et al. (2002), Soberon et al. (2007), and Diaz-Mendoza et al. (2007) contrast with those of Hofte et al. (1986), who reported that deletion of 36 amino acids from the N-terminus of Cry1Ab resulted in loss of insecticidal activity.

We have deduced the beginnings and ends of α-helix 1, α-helix 2A, α-helix 2B, and α-helix 3, and the location of the spacer regions between them in Domain I of the DIG-3 toxin by comparing the DIG-3 protein sequence with the protein sequence for Cry8Ea1, for which the structure is known. These locations are described in Table 1.

TABLE 1

Amino acid coordinates of projected α-helices of DIG-3 protein.

| | α-helix 1 | spacer | α-helix 2A | spacer | α-helix 2B | spacer | α-helix 3 |
|---|---|---|---|---|---|---|---|
| Residues of SEQ ID NO: 2 | 53-70 | 71-76 | 77-91 | 92-99 | 100-108 | 109-113 | 114-138 |

Amino terminal deletion variants of DIG-3. In one of its aspects the invention provides DIG-3 variants in which all or part of α-helix 1, α-helix 2A, and α-helix 2B are deleted to improve insecticidal activity and avoid development of resistance by insects. These modifications are made to provide DIG-3 variants with improved attributes, such as improved target pest spectrum, potency, and insect resistance management. In some embodiments of the invention, the subject modifications may affect the efficiency of protoxin activation and pore formation, leading to insect intoxication. More specifically, to provide DIG-3 variants with improved attributes, step-wise deletions are described that remove part of the nucleic acid sequence encoding the N-terminus of the DIG-3 protein. The deletions remove all of α-helix 1 and all or part of α-helix 2 in Domain I, while maintaining the structural integrity of α-helices 3 through 7. The subject invention therefore relates in part to improvements to Cry protein efficacy made by engineering the α-helical components of Domain 1 for more efficient pore formation. More specifically, the subject invention relates in part to improved DIG-3 proteins designed to have N-terminal deletions in regions with putative secondary structure homology to α-helix 1 and α-helix 2 in Domain I of Cry1 proteins.

Deletions to improve the insecticidal properties of the DIG-3 toxins may initiate before the predicted α-helix 2A start, and may terminate after the α-helix 2B end, but preferably do not extend into α-helix 3.

In designing coding sequences for the N-terminal deletion variants, an ATG start codon, encoding methionine, is inserted at the 5' end of the nucleotide sequence designed to encode the deletion variant. For sequences designed for use in transgenic plants, it may be of benefit to adhere to the "N-end rule" of Varshavsky (1997). It is taught that some amino acids may contribute to protein instability and degradation in eukaryotic cells when displayed as the N-terminal residue of a protein. For example, data collected from observations in yeast and mammalian cells indicate that the N-terminal destabilizing amino acids are F, L, W, Y, R, K, H, I, N, Q, D, E and possibly P. While the specifics of protein degradation mechanisms may differ somewhat between organisms, the conservation of identity of N-terminal destabilizing amino acids seen above suggests that similar mechanisms may function in plant cells. For instance, Worley et al. (1998) found that in plants, the N-end rule includes basic and aromatic residues. It is a possibility that proteolytic cleavage by plant proteases near the start of α-helix 3 of subject B.t. insecticidal proteins may expose a destabilizing N-terminal amino acid. Such processing may target the cleaved proteins for rapid decay and limit the accumulation of the B.t. insecticidal proteins to levels insufficient for effective insect control. Accordingly, for N-terminal deletion variants that begin with one of the destabilizing amino acids, applicants prefer to add a codon that specifies a G (glycine) amino acid between the translational initiation methionine and the destabilizing amino acid.

Example 2 gives specific examples of amino-terminal deletion variants of DIG-3 in accordance with the invention. Additional useful fragments that retain toxicity can be identified by trypsin or chymotrypsin digestion of the full length solubilized crystal protein. Further examples of toxic DIG-3 protein fragments may be encoded by fragments of the DIG-3 coding region. Insect active DIG-3 variants will mostly have a short N-terminal truncation and a long C-terminal truncation. The N-terminal end of the smallest toxic fragment is conveniently determined by N-terminal amino acid sequence determination of trypsin- or chymotrypsin-treated soluble crystal protein by techniques routinely available in the art.

Chimeric Toxins. Chimeric proteins utilizing the core toxin segment of one Cry toxin fused to the protoxin segment of another Cry toxin have previously been reported. DIG-3 variants include toxins comprising an N-terminal core toxin segment of a DIG-3 toxin (which may be full length or have the N-terminal deletions described above) fused to a heterologous protoxin segment at some point past the end of the core toxin segment. The transition to the heterologous protoxin segment can occur at approximately the native core toxin/protoxin junction or, in the alternative, a portion of the native protoxin (extending past the core toxin segment) can be retained with the transition to the heterologous protoxin occurring downstream. As an example, a chimeric toxin of the subject invention has the full core toxin segment of DIG-3 (amino acids 1-643) and a heterologous protoxin segment (amino acids 643 to the C-terminus). In a preferred embodiment, the heterologous protoxin segment is derived from a Cry1Ab delta-endotoxin, as illustrated in SEQ ID NO:5.

SEQ ID NO:4 discloses the 545 amino acid sequence of a Cry1Ab protoxin segment useful in DIG-3 variants of the invention. Attention is drawn to the last about 100 to 150 amino acids of this protoxin segment, which it is most critical to include in the chimeric toxin of the subject invention.

Protease sensitivity variants. Insect gut proteases typically function in aiding the insect in obtaining needed amino acids from dietary protein. The best understood insect digestive proteases are serine proteases, which appear to be the most common type (Englemann and Geraerts (1980), particularly in Lepidopteran species. Coleopteran insects have guts that are more neutral to acidic than are Lepidopteran guts. The majority of Coleopteran larvae and adults, for example Colorado potato beetle, have slightly acidic midguts, and cysteine proteases provide the major proteolytic activity (Wolfson and Murdock, 1990). More precisely, Thie and Houseman (1990) identified and characterized the cysteine proteases, cathepsin B-like and cathepsin H-like, and the aspartyl protease, cathepsin D-like, in Colorado potato beetle. Gillikin et al. (1992) characterized the proteolytic activity in the guts of western corn rootworm larvae and found primarily cysteine proteases. U.S. Pat. No. 7,230,167 disclosed that a protease activity attributed to cathepsin G exists in western corn rootworm. The diversity and different activity levels of the insect gut proteases may influence an insect's sensitivity to a particular B.t. toxin.

In another embodiment of the invention, protease cleavage sites may be engineered at desired locations to affect protein processing within the midgut of susceptible larvae of certain insect pests. These protease cleavage sites may be introduced by methods such as chemical gene synthesis or splice overlap PCR (Horton et al., 1989). Serine protease recognition sequences, for example, can optionally be inserted at specific sites in the Cry protein structure to effect protein processing at desired deletion points within the midgut of susceptible larvae. Serine proteases that can be exploited in such fashion include Lepidopteran midgut serine proteases such as trypsin or trypsin-like enzymes, chymotrypsin, elastase, etc. (Christeller et al., 1992). Further, deletion sites identified empirically by sequencing Cry protein digestion products generated with unfractionated larval midgut protease preparations or by binding to brush border membrane vesicles can be engineered to effect protein activation. Modified Cry proteins generated either by gene deletion or by introduction of protease cleavage sites have improved activity on Lepidopteran pests including *Ostrinia nubilalis*, *Diatraea grandiosella*, *Helicoverpa zea*, *Agrotis ipsilon*, *Spodoptera frugiperda*, *Spodoptera exigua*, *Diatraea saccharalis*, *Loxagrotis albicosta*, and other target pests.

Coleopteran serine proteases such as trypsin, chymotrypsin and cathepsin G-like protease, Coleopteran cysteine proteases such as cathepsins (B-like, L-like, O-like, and K-like proteases) (Koiwa et al., (2000) and Bown et al., (2004)], Coleopteran metalloproteases such as ADAM10 [Ochoa-Campuzano et al., (2007)), and Coleopteran aspartic acid proteases such as cathepsins D-like and E-like, pepsin, plasmepsin, and chymosin may further be exploited by engineering appropriate recognition sequences at desired processing sites to affect Cry protein processing within the midgut of susceptible larvae of certain insect pests.

A preferred location for the introduction of such protease cleavage sites may be within the "spacer" region between α-helix 2B and α-helix 3, for example within amino acids 109 to 113 of the full length DIG-3 protein (SEQ ID NO:2 and Table 1). Modified Cry proteins generated either by gene deletion or by introduction of protease cleavage sites have improved activity on insect pests including but not limited to western corn rootworm, southern corn root worn, northern corn rootworm, and the like.

Various technologies exist to enable determination of the sequence of the amino acids which comprise the N-terminal or C-terminal residues of polypeptides. For example, automated Edman degradation methodology can be used in sequential fashion to determine the N-terminal amino acid sequence of up to 30 amino acid residues with 98% accuracy per residue. Further, determination of the sequence of the amino acids comprising the carboxy end of polypeptides is also possible [Bailey et al., (1992); U.S. Pat. No. 6,046,053]. Thus, in some embodiments, B.t. Cry proteins which have been activated by means of proteolytic processing, for example, by proteases prepared from the gut of an insect, may be characterized and the N-terminal or C-terminal amino acids of the activated toxin fragment identified. DIG-3 variants produced by introduction or elimination of protease processing sites at appropriate positions in the coding sequence to allow, or eliminate, proteolytic cleavage of a larger variant protein by insect, plant or microorganism proteases are within the scope of the invention. The end result of such manipulation is understood to be the generation of toxin fragment molecules having the same or better activity as the intact (full length) toxin protein.

Domains of the DIG-3 toxin. The separate domains of the DIG-3 toxin, (and variants that are 90%, 95%, or 97% identical to such domains) are expected to be useful in forming combinations with domains from other Cry toxins to provide new toxins with increased spectrum of pest toxicity, improved potency, or increased protein stability. Domain I of the DIG-3 protein consists of amino acid residues 56 to 278 of SEQ ID NO:2. Domain II of the DIG-3 protein consists of amino acid residues 283 to 493 of SEQ ID NO:2. Domain III of the DIG-3 protein consists of amino acid residues 503 to 641 of SEQ ID NO:2. Domain swapping or shuffling is a mechanism for generating altered delta-endotoxin proteins. Domains II and III may be swapped between delta-endotoxin proteins, resulting in hybrid or chimeric toxins with improved pesticidal activity or target spectrum. Domain II is involved in receptor binding, and the DIG-3 Domain II is very divergent from other Cry1B toxins. Domain III binds certain classes of receptor proteins and perhaps participates in insertion of an oligomeric toxin pre-pore. Some Domain III substitutions in other toxins have been shown to produce superior toxicity against *Spodoptera exigua* (de Maagd et al., 1996), and guidance exists on the design of the Cry toxin domain swaps (Knight et al., 2004).

Methods for generating recombinant proteins and testing them for pesticidal activity are well known in the art (see, for example, Naimov et al., (2001), de Maagd et al., (1996), Ge et al., (1991), Schnepf et al., (1990), Rang et al., (1999)). Domain I from Cry1A and Cry3A proteins has been studied for the ability to insert and form pores in membranes. α-helix 4 and α-helix 5 of Domain I play key roles in membrane insertion and pore formation [Walters et al., (1993), Gazit et al., (1998); Nunez-Valdez et al., (2001)], with the other alpha helices proposed to contact the membrane surface like the ribs of an umbrella (Bravo et al., (2007); Gazit et al., (1998)).

DIG-3 variants created by making a limited number of amino acid deletions, substitutions, or additions. Amino acid deletions, substitutions, and additions to the amino acid sequence of SEQ ID NO:2 can readily be made in a sequential manner and the effects of such variations on insecticidal activity can be tested by bioassay. Provided the number of changes is limited in number, such testing does not involve unreasonable experimentation. The invention includes insecticidally active variants of the core toxin segment (amino acids 1-643 of SEQ ID NO:2, or amino acids 73-643 of SEQ ID NO:2) in which up to 10, up to 15, or up to 20 independent amino acid additions, deletions, or substitutions have been made.

The invention includes DIG-3 variants having a core toxin segment that is 90%, 95% or 97% identical to amino acids 1-643 of SEQ ID NO:2 or amino acids 73-643 of SEQ ID NO:2.

Variants may be made by making random mutations or the variants may be designed. In the case of designed mutants, there is a high probability of generating variants with similar activity to the native toxin when amino acid identity is maintained in critical regions of the toxin which account for biological activity or are involved in the determination of three-dimensional configuration which ultimately is responsible for the biological activity. A high probability of retaining activity will also occur if substitutions are conservative. Amino acids may be placed in the following classes: nonpolar, uncharged polar, basic, and acidic. Conservative substitutions whereby an amino acid of one class is replaced with another amino acid of the same type are least likely to materially alter the biological activity of the variant. Table 2 provides a listing of examples of amino acids belonging to each class.

TABLE 2

| Class of Amino Acid | Examples of Amino Acids |
| --- | --- |
| Nonpolar Side Chains | Ala (A), Val (V), Leu (L), Ile (I), Pro (P), Met (M), Phe (F), Trp (W) |
| Uncharged Polar Side Chains | Gly (G), Ser (S), Thr (T), Cys (C), Tyr (Y), Asn (N), Gln (Q) |
| Acidic Side Chains | Asp (D), Glu (E) |
| Basic Side Chains | Lys (K), Arg (R), His (H) |
| Beta-branched Side Chains | Thr, Val, Ile |
| Aromatic Side Chains | Tyr, Phe, Trp, His |

In some instances, non-conservative substitutions can also be made. The critical factor is that these substitutions must not significantly detract from the biological activity of the toxin. Variants include polypeptides that differ in amino acid sequence due to mutagenesis. Variant proteins encompassed by the present invention are biologically active, that is they continue to possess the desired biological activity of the native protein, namely, retaining pesticidal activity.

Variant proteins can also be designed that differ at the sequence level but that retain the same or similar overall essential three-dimensional structure, surface charge distribution, and the like. See e.g. U.S. Pat. No. 7,058,515; Larson et al. (2002); Stemmer (1994a,1994b, 1995); and Crameri et al. (1996a, 1996b, 1997).

Nucleic Acids. Isolated nucleic acids encoding DIG-3 toxins are one aspect of the present invention. This includes nucleic acids encoding SEQ ID NO:2 and SEQ ID NO:5, and complements thereof, as well as other nucleic acids that encode insecticidal variants of SEQ ID NO:2. Because of the redundancy of the genetic code, a variety of different DNA sequences can encode the amino acid sequences disclosed herein. It is well within the skill of a person trained in the art to create these alternative DNA sequences encoding the same, or essentially the same, toxins.

Gene synthesis. DNA sequences encoding the improved Cry proteins described herein can be made by a variety of methods well-known in the art. For example, synthetic gene segments and synthetic genes can be made by phosphite tri-ester and phosphoramidite chemistry (Caruthers et al., 1987), and commercial vendors are available to perform DNA synthesis on demand. Sequences encoding full-length DIG-3 proteins can be assembled in a variety of ways including, for example, by ligation of restriction fragments or polymerase chain reaction assembly of overlapping oligonucleotides (Stewart and Burgin, 2005). Further, sequences encoding terminal deletions can be made by PCR amplification using site-specific terminal oligonucleotides.

Nucleic acids encoding DIG-3 toxins can be made for example, by synthetic construction by methods currently practiced by any of several commercial suppliers. (See for example, U.S. Pat. No. 7,482,119 B2). These nucleic acids, or portions or variants thereof, may also be constructed synthetically, for example, by use of a gene synthesizer and the design methods of, for example, U.S. Pat. No. 5,380,831. Alternatively, variations of synthetic or naturally occurring genes may be readily constructed using standard molecular biological techniques for making point mutations. Fragments of these genes can also be made using commercially available exonucleases or endonucleases according to standard procedures. For example, enzymes such as Bal31 or site-directed mutagenesis can be used to systematically cut off nucleotides from the ends of these genes. Also, gene fragments which encode active toxin fragments may be obtained using a variety of restriction enzymes.

Given the amino acid sequence for a DIG-3 toxin, a coding sequence can be designed by reverse translating the coding sequence using codons preferred by the intended host, and then refining the sequence using alternative codons to remove sequences that might cause problems and provide periodic stop codons to eliminate long open coding sequences in the non-coding reading frames.

Quantifying Sequence Identity. To determine the percent identity of two amino acid sequences or of two nucleic acid sequences, the sequences are aligned for optimal comparison purposes. The percent identity between the two sequences is a function of the number of identical positions shared by the sequences (i.e. percent identity=number of identical positions/total number of positions (e.g. overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of such an algorithm is that of Karlin and Altschul (1990), modified as in Karlin and Altschul (1993), and incorporated into the BLASTN and BLASTX programs. BLAST searches may be conveniently used to identify sequences homologous (similar) to a query sequence in nucleic or protein databases. BLASTN searches can be performed, (score=100, word length=12) to identify nucleotide sequences having homology to claimed nucleic acid molecules of the invention. BLASTX searches can be performed (score=50, word length=3) to identify amino acid sequences having homology to claimed insecticidal protein molecules of the invention.

Gapped BLAST (Altschul et al., 1997) can be utilized to obtain gapped alignments for comparison purposes, Alternatively, PSI-Blast can be used to perform an iterated search that detects distant relationships between molecules (Altschul et al., 1997). When utilizing BLAST, Gapped BLAST, and PSI-Blast programs, the default parameters of the respective programs can be used. See www.ncbi.nlm.nih.gov.

A non-limiting example of a mathematical algorithm utilized for the comparison of sequences is the ClustalW algorithm (Thompson et al., 1994). ClustalW compares sequences and aligns the entirety of the amino acid or DNA sequence, and thus can provide data about the sequence conservation of the entire amino acid sequence or nucleotide sequence. The ClustalW algorithm is used in several commercially available DNA/amino acid analysis software packages, such as the ALIGNX module of the Vector NTI Program Suite (Invitrogen, Inc., Carlsbad, Calif.). When aligning amino acid sequences with ALIGNX, one may conveniently use the default settings with a Gap open penalty of 10, a Gap extend penalty of 0.1 and the blosum63mt2 comparison matrix to assess the percent amino acid similarity (consensus) or identity between the two sequences. When aligning DNA sequences with ALIGNX, one may conveniently use the default settings with a Gap open penalty of 15, a Gap extend penalty of 6.6 and the swgapdnamt comparison matrix to assess the percent identity between the two sequences.

Another non-limiting example of a mathematical algorithm utilized for the comparison of sequences is that of Myers and Miller (1988). Such an algorithm is incorporated into the wSTRETCHER program, which is part of the wEMBOSS sequence alignment software package (available at http://emboss.sourceforge.net/). wSTRETCHER calculates an optimal global alignment of two sequences using a modification of the classic dynamic programming algorithm which uses linear space. The substitution matrix, gap insertion penalty and gap extension penalties used to calculate the alignment may be specified. When utilizing the wSTRETCHER program for comparing nucleotide sequences, a Gap open penalty of 16 and a Gap extend penalty of 4 can be used with the scoring matrix file EDNAFULL. When used for comparing amino acid sequences, a Gap open penalty of 12 and a Gap extend penalty of 2 can be used with the EBLOSUM62 scoring matrix file.

A further non-limiting example of a mathematical algorithm utilized for the comparison of sequences is that of Needleman and Wunsch (1970), which is incorporated in the sequence alignment software packages GAP Version 10 and wNEEDLE (http://emboss.sourceforge.net/). GAP Version 10 may be used to determine sequence identity or similarity using the following parameters: for a nucleotide sequence, % identity and % similarity are found using GAP Weight of 50 and Length Weight of 3, and the nwsgapdna. cmp scoring matrix. For amino acid sequence comparison, % identity or % similarity are determined using GAP weight of 8 and length weight of 2, and the BLOSUM62 scoring program.

wNEEDLE reads two input sequences, finds the optimum alignment (including gaps) along their entire length, and writes their optimal global sequence alignment to file. The algorithm explores all possible alignments and chooses the best, using .a scoring matrix that contains values for every possible residue or nucleotide match. wNEEDLE finds the alignment with the maximum possible score, where the score of an alignment is equal to the sum of the matches taken from the scoring matrix, minus penalties arising from opening and extending gaps in the aligned sequences. The substitution matrix and gap opening and extension penalties are user-specified. When amino acid sequences are compared, a default Gap open penalty of 10, a Gap extend penalty of 0.5, and the EBLOSUM62 comparison matrix are used. When DNA sequences are compared using wNEEDLE, a Gap open penalty of 10, a Gap extend penalty of 0.5, and the EDNAFULL comparison matrix are used.

Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by ALIGNX, wNEEDLE, or wSTRETCHER. The % identity is the percentage of identical matches between the two sequences over the reported aligned region (including any gaps in the length) and the % similarity is the percentage of matches between the two sequences over the reported aligned region (including any gaps in the length).

Alignment may also be performed manually by inspection.

Recombinant hosts. The toxin-encoding genes of the subject invention can be introduced into a wide variety of microbial or plant hosts. Expression of the toxin gene results, directly or indirectly, in the intracellular production and maintenance of the pesticidal protein. With suitable microbial hosts, e.g. *Pseudomonas*, the microbes can be applied to the environment of the pest, where they will proliferate and be ingested. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type indigenous microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g. genera *Pseudomonas, Erwinia, Serratia, Klebsiella, Xanthomonas, Streptomyces, Rhizobium, Sinorhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g. genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Agrobacterium radiobacter, Rhodopseudomonas spheroides, Xanthomonas campestris, Sinorhizobium meliloti* (formerly *Rhizobium meliloti*), *Alcaligenes eutrophus*, and *Azotobacter vinelandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

Methods of Controlling Insect Pests

When an insect comes into contact with an effective amount of toxin delivered via transgenic plant expression, formulated protein compositions(s), sprayable protein composition(s), a bait matrix or other delivery system, the results are typically death of the insect, or the insects do not feed upon the source which makes the toxins available to the insects.

The subject protein toxins can be "applied" or provided to contact the target insects in a variety of ways. For example, transgenic plants (wherein the protein is produced by and present in the plant) can be used and are well-known in the art. Expression of the toxin genes can also be achieved selectively in specific tissues of the plants, such as the roots, leaves, etc. This can be accomplished via the use of tissue-specific promoters, for example. Spray-on applications are another example and are also known in the art. The subject proteins can be appropriately formulated for the desired end use, and then sprayed (or otherwise applied) onto the plant and/or around the plant/to the vicinity of the plant to be protected—before an infestation is discovered, after target insects are discovered, both before and after, and the like. Bait granules, for example, can also be used and are known in the art.

Transgenic Plants

The subject proteins can be used to protect practically any type of plant from damage by a Lepidopteran insect. Nonlimiting examples of such plants include maize, sunflower, soybean, cotton, canola, rice, sorghum, wheat, barley, vegetables, ornamentals, peppers (including hot peppers), sugar beets, fruit, and turf, to name but a few. Methods for transforming plants are well known in the art, and illustrative transformation methods are described in the Examples.

A preferred embodiment of the subject invention is the transformation of plants with genes encoding the subject insecticidal protein or its variants. The transformed plants are resistant to attack by an insect target pest by virtue of the presence of controlling amounts of the subject insecticidal protein or its variants in the cells of the transformed plant. By incorporating genetic material that encodes the insecticidal properties of the B.t. insecticidal toxins into the genome of a plant eaten by a particular insect pest, the adult or larvae would die after consuming the food plant. Numerous members of the monocotyledonous and dicotyledonous classifications have been transformed. Transgenic agronomic crops as well as fruits and vegetables are of commercial interest. Such crops include, but are not limited to, maize, rice, soybeans, canola, sunflower, alfalfa, sorghum, wheat, cotton, peanuts, tomatoes, potatoes, and the like. Several techniques exist for introducing foreign genetic material into plant cells, and for obtaining plants that stably maintain and express the introduced gene. Such techniques include acceleration of genetic material coated onto microparticles directly into cells (U.S. Pat. No. 4,945,050 and U.S. Pat. No. 5,141,131). Plants may be transformed using *Agrobacterium* technology, see U.S. Pat. No. 5,177,010, U.S. Pat. No. 5,104,310, European Patent Application No. 0131624B1, European Patent Application No. 120516, European Patent Application No. 159418B1, European Patent Application No. 176112, U.S. Pat. Nos. 5,149,645, 5,469,976, 5,464,763, 4,940,838, 4,693,976, European Patent Application No. 116718, European Patent Application No. 290799, European Patent Application No. 320500, European Patent Application No. 604662, European Patent Application No. 627752, European Patent Application No. 0267159, European Patent Application No. 0292435, U.S. Pat. Nos. 5,231,019, 5,463,174, 4,762,785, 5,004,863, and 5,159,135. Other transformation technology includes WHISKERS™ technology, see U.S. Pat. Nos. 5,302,523 and 5,464,765. Electroporation technology has also been used to transform plants, see WO 87/06614, U.S. Pat. Nos. 5,472,869, 5,384,253, WO 9209696, and WO 9321335. All of these transformation patents and publications are incorporated by reference. In addition to numerous technologies for transforming plants, the type of tissue which is contacted with the foreign genes may vary as well. Such tissue would include but would not be limited to embryogenic tissue, callus tissue types I and II, hypocotyl, meristem, and the like. Almost all plant tissues may be transformed during dedifferentiation using appropriate techniques within the skill of an artisan.

Genes encoding DIG-3 toxins can be inserted into plant cells using a variety of techniques which are well known in the art as disclosed above. For example, a large number of cloning vectors comprising a marker that permits selection of the transformed microbial cells and a replication system functional in *Escherichia coli* are available for preparation and modification of foreign genes for insertion into higher plants. Such manipulations may include, for example, the insertion of mutations, truncations, additions, or substitutions as desired for the intended use. The vectors comprise, for example, pBR322, pUC series, M13 mp series, pACYC184, etc. Accordingly, the sequence encoding the Cry protein or variants can be inserted into the vector at a suitable restriction site. The resulting plasmid is used for transformation of cells of *E. coli*, the cells of which are cultivated in a suitable nutrient medium, then harvested and lysed so that workable quantities of the plasmid are recovered. Sequence analysis, restriction fragment analysis, electrophoresis, and other biochemical-molecular biological methods are generally carried out as methods of analysis. After each manipulation, the DNA sequence used can be cleaved and joined to the next DNA sequence. Each manipulated DNA sequence can be cloned in the same or other plasmids.

The use of T-DNA-containing vectors for the transformation of plant cells has been intensively researched and sufficiently described in EP 120516; Lee and Gelvin (2008), Fraley et al. (1986), and An et al. (1985), and is well established in the field.

Once the inserted DNA has been integrated into the plant genome, it is relatively stable throughout subsequent generations. The vector used to transform the plant cell normally contains a selectable marker gene encoding a protein that confers on the transformed plant cells resistance to a herbicide or an antibiotic, such as bialaphos, kanamycin, G418, bleomycin, or hygromycin, inter alfa. The individually employed selectable marker gene should accordingly permit the selection of transformed cells while the growth of cells that do not contain the inserted DNA is suppressed by the selective compound.

A large number of techniques are available for inserting DNA into a host plant cell. Those techniques include transformation with T-DNA delivered by *Agrobacterium tumefaciens* or *Agrobacterium rhizogenes* as the transformation agent. Additionally, fusion of plant protoplasts with liposomes containing the DNA to be delivered, direct injection of the DNA, biolistics transformation (microparticle bombardment), or electroporation, as well as other possible methods, may be employed.

In a preferred embodiment of the subject invention, plants will be transformed with genes wherein the codon usage of the protein coding region has been optimized for plants. See, for example, U.S. Pat. No. 5,380,831, which is hereby incorporated by reference. Also, advantageously, plants encoding a truncated toxin will be used. The truncated toxin typically will encode about 55% to about 80% of the full length toxin. Methods for creating synthetic B.t. genes for use in plants are known in the art (Stewart, 2007).

Regardless of transformation technique, the gene is preferably incorporated into a gene transfer vector adapted to express the B.t insecticidal toxin genes and variants in the plant cell by including in the vector a plant promoter. In addition to plant promoters, promoters from a variety of sources can be used efficiently in plant cells to express foreign genes. For example, one may use promoters of bacterial origin, such as the octopine synthase promoter, the nopaline synthase promoter, and the mannopine synthase promoter. Promoters of plant virus origin may be used, for example, the 35S and 19S promoters of Cauliflower Mosaic Virus, a promoter from Cassaya Vein Mosaic Virus, and the like. Plant promoters include, but are not limited to, ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, ubiquitin promoter, actin promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g., actin, ubiquitin, CaMV 35S). Tissue specific promoters are responsible for gene expression in specific cell or tissue types, such as the leaves or seeds (e.g. zein, oleosin, napin, ACP (Acyl Carrier Protein) promoters), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Under certain circumstances it may be desirable to use an inducible promoter. An inducible promoter is responsible for expression of genes in response to a specific signal, such as: physical stimulus (e.g. heat shock genes); light (e.g. RUBP carboxylase); hormone (e.g. glucocorticoid); antibiotic (e.g. tetracycline); metabolites; and stress (e.g. drought). Other desirable transcription and translation elements that function in plants may be used, such as 5' untranslated leader sequences, RNA transcription termination sequences and poly-adenylate addition signal sequences. Numerous plant-specific gene transfer vectors are known to the art.

Transgenic crops containing insect resistance (IR) traits are prevalent in corn and cotton plants throughout North America, and usage of these traits is expanding globally. Commercial transgenic crops combining IR and herbicide tolerance (HT) traits have been developed by multiple seed companies. These include combinations of IR traits conferred by B.t. insecticidal proteins and HT traits such as tolerance to Acetolactate Synthase (ALS) inhibitors such as sulfonylureas, imidazolinones, triazolopyrimidine, sulfonanilides, and the like, Glutamine Synthetase (GS) inhibitors such as bialaphos, glufosinate, and the like, 4-HydroxyPhenylPyruvate Dioxygenase (HPPD) inhibitors such as mesotrione, isoxaflutole, and the like, 5-EnolPyruvylShikimate-3-Phosphate Synthase (EPSPS) inhibitors such as glyphosate and the like, and Acetyl-Coenzyme A Carboxylase (ACCase) inhibitors such as haloxyfop, quizalofop, diclofop, and the like. Other examples are known in which transgenically provided proteins provide plant tolerance to herbicide chemical classes such as phenoxy acids herbicides and pyridyloxyacetates auxin herbicides (see WO 2007/053482 A2), or phenoxy acids herbicides and aryloxyphenoxypropionates herbicides (see WO 2005107437 A2, A3). The ability to control multiple pest problems through IR traits is a valuable commercial product concept, and the convenience of this product concept is enhanced if insect control traits and weed control traits are combined in the same plant. Further, improved value may be obtained via single plant combinations of IR traits conferred by a B.t. insecticidal protein such as that of the subject invention, with one or more additional HT traits such as those mentioned above, plus one or more additional input traits (e.g. other insect resistance conferred by B.t.-derived or other insecticidal proteins, insect resistance conferred by mechanisms such as RNAi and the like, nematode resistance, disease resistance, stress tolerance, improved nitrogen utilization, and the like), or output traits (e.g. high oils content, healthy oil composition, nutritional improvement, and the like). Such combinations may be obtained either through conventional breeding (breeding stack) or jointly as a novel transformation event involving the simultaneous introduction of multiple genes (molecular stack). Benefits include the ability to manage insect pests and improved weed control in a crop plant that provides secondary benefits to the producer and/or the consumer. Thus, the subject invention can be used in combination with other traits to provide a complete agronomic package of improved crop quality with the ability to flexibly and cost effectively control any number of agronomic issues.

Target Pests

The DIG-3 toxins of the invention are particularly suitable for use in control of Lepidopteran insects. Lepidopterans are an important group of agricultural, horticultural, and household pests which cause a very large amount of damage each year. This insect order encompasses foliar- and root-feeding larvae and adults. Lepidopteran insect pests include, but are not limited to: *Achoroia grisella, Acleris gloverana, Acleris variana, Adoxophyes orana, Agrotis Ipsilon* (black cutworm), *Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmia feneralis, Diaphania hyalinata, Diaphania nitidalis, Diatraea grandiosella* (southwestern corn borer), *Diatraea saccharalis* (sugarcane borer), *Ennomos subsignaria, Eoreuma loftini, Esphestia elutella, Erannis tiliaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea* (corn earworm), *Heliothis virescens* (tobacco budworm), *Hemileuca oliviae, Homoeosoma electellum* (sunflower head moth), *Hyphantia cunea, Keiferia lycopersicella, Lambdina fiscellaria fiscellaria, Lambdina fiscellaria lugubrosa, Leucoma salicis, Lobesia botrana, Loxagrotis albicosta* (western bean cutworm), *Loxostege sticticalis, Lymantria dispar, Macalla thyrisalis, Malacosoma* sp., *Mamestra brassicae, Mamestra configurata* (bertha armyworm), *Manduca quinquemaculata, Manduca sexta* (tobacco hornworm), *Maruca testulalis, Melanchra picta, Operophtera brumata, Orgyia* sp., *Ostrinia nubilalis* (European corn borer), *Paleacrita vernata, Papiapema nebris* (common stalk borer), *Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella* (diamondback moth), *Pontia protodice, Pseudaletia unipuncta* (armyworm), *Pseudoplasia includens, Rachiplusia nu* (Argentine looper), *Sabulodes aegrotata, Schizura concinna, Sitotroga cerealella, Spilonta ocellana, Spodoptera frugiperda* (fall armyworm), *Spodoptera exigua* (beet armyworm), *Thaurnstopoea pityocampa, Ensola bisselliella, Trichoplusia hi, Udea rubigalis, Xylomyges curiails*, and *Yponomeuta padella*.

Use of DIG-3 toxins to control Coleopteran pests of crop plants is also contemplated. In some embodiments, Cry proteins may be economically deployed for control of insect pests that include but are not limited to, for example, rootworms such as *Diabrotica undecimpunctata howardi* (southern corn rootworm), *Diabrotica longicornis barberi* (northern corn rootworm), and *Diabrotica virgifera* (western corn rootworm), and grubs such as the larvae of *Cyclocephala*

*borealis* (northern masked chafer), *Cyclocephala immaculate* (southern masked chafer), and *Popillia japonica* (Japanese beetle).

Use of the DIG-3 toxins to control parasitic nematodes including, but not limited to, root knot nematode (*Meloidogyne icognita*) and soybean cyst nematode (*Heterodera glycines*) is also contemplated.

Antibody Detection of DIG-3 Toxins

Anti-toxin antibodies. Antibodies to the toxins disclosed herein, or to equivalent toxins, or fragments of these toxins, can readily be prepared using standard procedures in this art. Such antibodies are useful to detect the presence of the DIG-3 toxins.

Once the B.t. insecticidal toxin has been isolated, antibodies specific for the toxin may be raised by conventional methods that are well known in the art. Repeated injections into a host of choice over a period of weeks or months will elicit an immune response and result in significant anti-B.t toxin serum titers. Preferred hosts are mammalian species and more highly preferred species are rabbits, goats, sheep and mice. Blood drawn from such immunized animals may be processed by established methods to obtain antiserum (polyclonal antibodies) reactive with the B.t. insecticidal toxin. The antiserum may then be affinity purified by adsorption to the toxin according to techniques known in the art. Affinity purified antiserum may be further purified by isolating the immunoglobulin fraction within the antiserum using procedures known in the art. The resulting material will be a heterogeneous population of immunoglobulins reactive with the B.t. insecticidal toxin.

Anti-B.t. toxin antibodies may also be generated by preparing a semi-synthetic immunogen consisting of a synthetic peptide fragment of the B.t. insecticidal toxin conjugated to an immunogenic carrier. Numerous schemes and instruments useful for making peptide fragments are well known in the art. Many suitable immunogenic carriers such as bovine serum albumin or keyhole limpet hemocyanin are also well known in the art, as are techniques for coupling the immunogen and carrier proteins. Once the semi-synthetic immunogen has been constructed, the procedure for making antibodies specific for the B.t. insecticidal toxin fragment is identical to those used for making antibodies reactive with natural B.t. toxin.

Anti-B.t. toxin monoclonal antibodies (MAbs) are readily prepared using purified B.t. insecticidal toxin. Methods for producing MAbs have been practiced for over 20 years and are well known to those of ordinary skill in the art. Repeated intraperitoneal or subcutaneous injections of purified B.t. insecticidal toxin in adjuvant will elicit an immune response in most animals. Hyperimmunized B-lymphocytes are removed from the animal and fused with a suitable fusion partner cell line capable of being cultured indefinitely. Preferred animals whose B-lymphocytes may be hyperimmunized and used in the production of MAbs are mammals. More preferred animals are rats and mice and most preferred is the BALB/c mouse strain.

Numerous mammalian cell lines are suitable fusion partners for the production of hybridomas. Many such lines are available from the American Type Culture Collection (ATCC, Manassas, Va.) and commercial suppliers. Preferred fusion partner cell lines are derived from mouse myelomas and the HL-1® Friendly myeloma-653 cell line (Ventrex, Portland, Me.) is most preferred. Once fused, the resulting hybridomas are cultured in a selective growth medium for one to two weeks. Two well known selection systems are available for eliminating unfused myeloma cells, or fusions between myeloma cells, from the mixed hybridoma culture. The choice of selection system depends on the strain of mouse immunized and myeloma fusion partner used. The AAT selection system, described by Taggart and Samloff, (1983), may be used; however, the HAT (hypoxanthine, aminopterin, thymidine) selection system, described by Littlefield, (1964), is preferred because of its compatibility with the preferred mouse strain and fusion partner mentioned above. Spent growth medium is screened for immunospecific MAb secretion. Enzyme linked immunosorbent assay (ELISA) procedures are best suited for this purpose; though, radioimmunoassays adapted for large volume screening are also acceptable. Multiple screens designed to consecutively pare down the considerable number of irrelevant or less desired cultures may be performed. Cultures that secrete MAbs reactive with the B.t. insecticidal toxin may be screened for cross-reactivity with known B.t. insecticidal toxins. MAbs that preferentially bind to the preferred B.t. insecticidal toxin may be isotyped using commercially available assays. Preferred MAbs are of the IgG class, and more highly preferred MAbs are of the $IgG_1$ and $IgG_{2a}$ subisotypes.

Hybridoma cultures that secrete the preferred MAbs may be sub-cloned several times to establish monoclonality and stability. Well known methods for sub-cloning eukaryotic, non-adherent cell cultures include limiting dilution, soft agarose and fluorescence activated cell sorting techniques. After each subcloning, the resultant cultures preferably are re-assayed for antibody secretion and isotype to ensure that a stable preferred MAb-secreting culture has been established.

The anti-B.t. toxin antibodies are useful in various methods of detecting the claimed B.t. insecticidal toxin of the instant invention, and variants or fragments thereof. It is well known that antibodies labeled with a reporting group can be used to identify the presence of antigens in a variety of milieus. Antibodies labeled with radioisotopes have been used for decades in radioimmunoassays to identify, with great precision and sensitivity, the presence of antigens in a variety of biological fluids. More recently, enzyme labeled antibodies have been used as a substitute for radiolabeled antibodies in the ELISA assay. Further, antibodies immunoreactive to the B.t. insecticidal toxin of the present invention can be bound to an immobilizing substance such as a polystyrene well or particle and used in immunoassays to determine whether the B.t. toxin is present in a test sample.

Detection Using Nucleic Acid Probes

A further method for identifying the toxins and genes of the subject invention is through the use of oligonucleotide probes. These probes are detectable nucleotide sequences. These sequences may be rendered detectable by virtue of an appropriate radioactive label or may be made inherently fluorescent as described in, for example, U.S. Pat. No. 6,268,132. As is well known in the art, if the probe molecule and nucleic acid sample hybridize by forming strong base-pairing bonds between the two molecules, it can be reasonably assumed that the probe and sample have substantial sequence homology. Preferably, hybridization is conducted under stringent conditions by techniques well-known in the art, as described, for example, in Keller and Manak (1993). Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Nucleic Acid Hybridization

As is well known to those skilled in molecular biology, similarity of two nucleic acids can be characterized by their tendency to hybridize. As used herein the terms "stringent conditions" or "stringent hybridization conditions" are intended to refer to conditions under which a probe will hybridize (anneal) to its target sequence to a detectably greater degree than to other sequences (e.g. at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C. and a wash in 1× to 2× SSC (20× SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1× SSC at 55° C. to 60° C. Exemplary high stringency conditions include hybridization in 50% formamide, 1 M NaCl, 1% SDS at 37° C. and a wash in 0.1× SSC at 60° C. to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA/DNA hybrids, the thermal melting point ($T_m$) is the temperature (under defined ionic strength and pH at which 50% of a complementary target sequence hybridizes to a perfectly matched probe. $T_m$ is reduced by about 1° C. for each 1% of mismatching; thus, $T_m$, hybridization conditions, and/or wash conditions can be adjusted to facilitate annealing of sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, highly stringent conditions can utilize a hybridization and/or wash at 1° C., 2° C., 3° C., or 4° C. lower than the $T_m$; moderately stringent conditions can utilize a hybridization and/or wash at 6° C., 7° C., 8° C., 9° C., or 10° C. lower than the $T_m$, and low stringency conditions can utilize a hybridization and/or wash at 11° C., 12° C., 13° C., 14° C., 15° C., or 20° C. lower than the $T_m$.

$T_m$ (in ° C.) may be experimentally determined or may be approximated by calculation. For DNA-DNA hybrids, the $T_m$ can be approximated from the equation of Meinkoth and Wahl (1984):

$$T_m(°\,C.)=81.5°\,C.+16.6(\log M)+0.41(\%\,GC)-0.61(\%\,\text{formamide})-500/L;$$

where M is the molarity of monovalent cations, % GC is the percentage of guanosine and cytosine nucleotides in the DNA, % formamide is the percentage of formamide in the hybridization solution, and L is the length of the hybrid in base pairs.

Alternatively, the $T_m$ is described by the following formula (Beltz et al., 1983).

$$T_m(°\,C.)=81.5°\,C.+16.6(\log [Na+])+0.41(\%\,GC)-0.61(\%\,\text{formamide})-600/L$$

where [Na+] is the molarity of sodium ions, % GC is the percentage of guanosine and cytosine nucleotides in the DNA, % formamide is the percentage of formamide in the hybridization solution, and L is the length of the hybrid in base pairs.

Using the equations, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) and Ausubel et al. (1995) Also see Sambrook et al. (1989).

Hybridization of immobilized DNA on Southern blots with radioactively labeled gene-specific probes may be performed by standard methods Sambrook et al., supra.). Radioactive isotopes used for labeling polynucleotide probes may include 32P, 33P, 14C, or 3H. Incorporation of radioactive isotopes into polynucleotide probe molecules may be done by any of several methods well known to those skilled in the field of molecular biology. (See, e.g. Sambrook et al., supra.) In general, hybridization and subsequent washes may be carried out under stringent conditions that allow for detection of target sequences with homology to the claimed toxin encoding genes. For double-stranded DNA gene probes, hybridization may be carried out overnight at 20°-25° C. below the $T_m$ of the DNA hybrid in 6× SSPE, 5×Denhardt's Solution, 0.1% SDS, 0.1 mg/mL denatured DNA [20× SSPE is 3 M NaCl, 0.2 M NaHPO$_4$, and 0.02 M EDTA (ethylenediamine tetra-acetic acid sodium salt); 100×Denhardt's Solution is 20 gm/L Polyvinylpyrollidone, 20 gm/L Ficoll type 400 and 20 gm/L Bovine Serum Albumin (fraction V)].

Washes may typically be carried out as follows:
Twice at room temperature for 15 minutes in 1× SSPE, 0.1% SDS (low stringency wash).
Once at $T_m$-20° C. for 15 minutes in 0.2× SSPE, 0.1% SDS (moderate stringency wash).

For oligonucleotide probes, hybridization may be carried out overnight at 10°-20° C. below the $T_m$ of the hybrid in 6× SSPE, 5×Denhardt's solution, 0.1% SDS, 0.1 mg/mL denatured DNA. $T_m$ for oligonucleotide probes may be determined by the following formula (Suggs et al., 1981).

$$T_m(°\,C.)=2(\text{number of } T/A \text{ base pairs})+4(\text{number of } G/C \text{ base pairs})$$

Washes may typically be carried out as follows:
Twice at room temperature for 15 minutes 1× SSPE, 0.1% SDS (low stringency wash).
Once at the hybridization temperature for 15 minutes in 1× SSPE, 0.1% SDS (moderate stringency wash).

Probe molecules for hybridization and hybrid molecules formed between probe and target molecules may be rendered detectable by means other than radioactive labeling. Such alternate methods are intended to be within the scope of this invention.

All patents, patent applications, provisional applications, and publications referred to or cited herein are incorporated by reference in their entirety to the extent they are not inconsistent with the explicit teachings of this specification. Unless specifically indicated or implied, the terms "a", "an", and "the" signify "at least one" as used herein. By the use of the term "genetic material" herein, it is meant to include all genes, nucleic acid, DNA and RNA.

For designations of nucleotide residues of polynucleotides, DNA, RNA, oligonucleotides, and primers, and for designations of amino acid residues of proteins, standard IUPAC abbreviations are employed throughout this document. Nucleic acid sequences are presented in the standard 5' to 3' direction, and protein sequences are presented in the standard amino (N) terminal to carboxy (C) terminal direction.

Following are examples that illustrate procedures for practicing the invention. It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. All percentages are by weight and all solvent mixture proportions are by volume unless otherwise noted. All temperatures are in degrees Celsius.

EXAMPLE 1

Isolation of a Gene Encoding DIG-3 Toxin

Nucleic acid encoding the insecticidal Cry protein designated herein as DIG-3 was isolated from genomic DNA of B.t. strain PS46L by PCR using a degenerate forward primer that hybridized to bases 1286 to 1311 of SEQ ID NO:1, and a mismatched reverse primer that hybridized to the complement of bases 2480 to 2499 of SEQ ID NO:1. This pair of primers was used to amplify a fragment of 1214 bp, corresponding to nucleotides 1286 to 2499 of SEQ ID NO:1. This sequence was used as the anchor point to begin genome walking using methods adapted from the GenomeWalker™ Universal Kit (Clontech, Palo Alto, Calif.). The nucleic acid sequence of a fragment spanning the DIG-3 coding region was determined. SEQ ID NO:1 is the 3771 by nucleotide sequence encoding the full length DIG-3 protein. SEQ ID NO:2 is the amino acid sequence of the full length DIG-3 protein deduced from SEQ ID NO:1. It is noted that in *Bacillus* species, protein coding regions such as that of SEQ ID NO:1 may initiate with the TTG codon, which translationally represents the amino acid methionine.

EXAMPLE 2

Deletion of Domain I α-Helices from DIG-3

To improve the insecticidal properties of the DIG-3 toxin, serial, step-wise deletions are made, each of which removes part of the N-terminus of the DIG-3 protein. The deletions remove part or all of α-helix 1 and part or all of α-helix 2 in Domain I, while maintaining the structural integrity of α-helix 3 through α-helix 7.

Deletions were designed as follows. This example utilizes the full length chimeric DNA sequence encoding the full-length DIG-3 protein e.g. SEQ ID NO:1 and SEQ ID NO:2, respectively) to illustrate the design principles with 67 specific variants. It utilizes the chimeric sequence of SEQ ID NO:5 (DNA encoding DIG-3 core toxin segment fused to Cry1Ab protoxin segment) to provide an additional 67 specific variants. One skilled in the art will realize that other DNA sequences encoding all or an N-terminal portion of the DIG-3 protein may be similarly manipulated to achieve the desired result. To devise the first deleted variant coding sequence, all of the bases that encode α-helix 1 up to the codon for the proline residue near the beginning of α-helix 2A (i.e. P73 for the full length DIG-3 protein of SEQ ID NO:2), are removed. Thus, elimination of bases 1 to 216 of SEQ ID NO:1 removes the coding sequence for amino acids 1 to 72 of SEQ ID NO:2. Reintroduction of a translation initiating ATG (methionine) codon at the beginning (i.e. in front of the codon corresponding to amino acid 73 of the full length protein) provides for the deleted variant coding sequence comprising an open reading frame of 3555 bases which encodes a deleted variant DIG-3 protein comprising 1185 amino acids (i.e. methionine plus amino acids 73 to 1256 of the full-length DIG-3 protein). Serial, stepwise deletions that remove additional codons for a single amino acid corresponding to residues 73 to 112 of the full-length DIG-3 protein of SEQ ID NO:2 provide variants lacking part or all of α-helix 2A and α-helix 2B. Thus a second designed deleted variant coding sequence requires elimination of bases 1 to 219 of SEQ ID NO:1, thereby removing the coding sequence for amino acids 1-73. Restoration of a functional open reading frame is again accomplished by reintroduction of a translation initiation methionine codon at the beginning of the remaining coding sequence, thus providing for a second deleted variant coding sequence having an open reading frame of 3552 bases encoding a deleted variant DIG-3 protein comprising 1184 amino acids (i.e. methionine plus amino acids 74 to 1256 of the full-length DIG-3 protein). The last designed deleted variant coding sequence requires removal of bases 1 to 336 of SEQ ID NO:1, thus eliminating the coding sequence for amino acids 1 to 112, and, after reintroduction of a translation initiation methionine codon, providing a deletion variant coding sequence having an open reading frame of 3435 bases which encodes a deletion variant DIG-3 protein of 1145 amino acids (i.e. methionine plus amino acids 113 to 1256 of the full-length DIG-3 protein). As exemplified, after elimination of the deletion sequence, an initiator methionine codon is added to the beginning of the remaining coding sequence to restore a functional open reading frame. Also as described, an additional glycine codon is to be added between the methionine codon and the codon for the instability-determining amino acid in the instance that removal of the deleted sequence leaves exposed at the N-terminus of the remaining portion of the full-length protein one of the instability-determining amino acids as provided above.

Table 3 describes specific variants designed in accordance with the strategy described above.

TABLE 3

Deletion variant protein sequences of the full-length DIG-3 protein of SEQ ID NO: 2 and the fusion protein sequence of SEQ ID NO: 5.

| DIG-3 Deletion Variant | Residues added at NH2 terminus | Residues of SEQ ID NO: 2 | DIG-3 Deletion Variant | Residues added at NH2 terminus | Residues of SEQ ID NO: 5 |
|---|---|---|---|---|---|
| 1 | M | 73-1256 | 68 | M | 73-1188 |
| 2 | MG | 73-1256 | 69 | MG | 73-1188 |

TABLE 3-continued

Deletion variant protein sequences of the full-length DIG-3 protein of SEQ ID NO: 2 and the fusion protein sequence of SEQ ID NO: 5.

| DIG-3 Deletion Variant | Residues added at NH2 terminus | Residues of SEQ ID NO: 2 | DIG-3 Deletion Variant | Residues added at NH2 terminus | Residues of SEQ ID NO: 5 |
|---|---|---|---|---|---|
| 3 | M | 74-1256 | 70 | M | 74-1188 |
| 4 | MG | 74-1256 | 71 | MG | 74-1188 |
| 5 | M | 75-1256 | 72 | M | 75-1188 |
| 6 | M | 76-1256 | 73 | M | 76-1188 |
| 7 | M | 77-1256 | 74 | M | 77-1188 |
| 8 | M | 78-1256 | 75 | M | 78-1188 |
| 9 | MG | 78-1256 | 76 | MG | 78-1188 |
| 10 | M | 79-1256 | 77 | M | 79-1188 |
| 11 | M | 80-1256 | 78 | M | 80-1188 |
| 12 | M | 81-1256 | 79 | M | 81-1188 |
| 13 | MG | 81-1256 | 80 | MG | 81-1188 |
| 14 | M | 82-1256 | 81 | M | 82-1188 |
| 15 | MG | 82-1256 | 82 | MG | 82-1188 |
| 16 | M | 83-1256 | 83 | M | 83-1188 |
| 17 | M | 84-1256 | 84 | M | 84-1188 |
| 18 | MG | 84-1256 | 85 | MG | 84-1188 |
| 19 | M | 85-1256 | 86 | M | 85-1188 |
| 20 | MG | 85-1256 | 87 | MG | 85-1188 |
| 21 | M | 86-1256 | 88 | M | 86-1188 |
| 22 | M | 87-1256 | 89 | M | 87-1188 |
| 23 | M | 88-1256 | 90 | M | 88-1188 |
| 24 | M | 89-1256 | 91 | M | 89-1188 |
| 25 | MG | 89-1256 | 92 | MG | 89-1188 |
| 26 | M | 90-1256 | 93 | M | 90-1188 |
| 27 | MG | 90-1256 | 94 | MG | 90-1188 |
| 28 | M | 91-1256 | 95 | M | 91-1188 |
| 29 | MG | 91-1256 | 96 | MG | 91-1188 |
| 30 | M | 92-1256 | 97 | M | 92-1188 |
| 31 | M | 93-1256 | 98 | M | 93-1188 |
| 32 | M | 94-1256 | 99 | M | 94-1188 |
| 33 | M | 95-1256 | 100 | M | 95-1188 |
| 34 | MG | 95-1256 | 101 | MG | 95-1188 |
| 35 | M | 96-1256 | 102 | M | 96-1188 |
| 36 | MG | 96-1256 | 103 | MG | 96-1188 |
| 37 | M | 97-1256 | 104 | M | 97-1188 |
| 38 | MG | 97-1256 | 105 | MG | 97-1188 |
| 39 | M | 98-1256 | 106 | M | 98-1188 |
| 40 | MG | 98-1256 | 107 | MG | 98-1188 |
| 41 | M | 99-1256 | 108 | M | 99-1188 |
| 42 | MG | 99-1256 | 109 | MG | 99-1188 |
| 43 | M | 100-1256 | 110 | M | 100-1188 |
| 44 | MG | 100-1256 | 111 | MG | 100-1188 |
| 45 | M | 101-1256 | 112 | M | 101-1188 |
| 46 | MG | 101-1256 | 113 | MG | 101-1188 |
| 47 | M | 102-1256 | 114 | M | 102-1188 |
| 48 | MG | 102-1256 | 115 | MG | 102-1188 |
| 49 | M | 103-1256 | 116 | M | 103-1188 |
| 50 | MG | 103-1256 | 117 | MG | 103-1188 |
| 51 | M | 104-1256 | 118 | M | 104-1188 |
| 52 | M | 105-1256 | 119 | M | 105-1188 |
| 53 | MG | 105-1256 | 120 | MG | 105-1188 |
| 54 | M | 106-1256 | 121 | M | 106-1188 |
| 55 | MG | 106-1256 | 122 | MG | 106-1188 |
| 56 | M | 107-1256 | 123 | M | 107-1188 |
| 57 | MG | 107-1256 | 124 | MG | 107-1188 |
| 58 | M | 108-1256 | 125 | M | 108-1188 |
| 59 | MG | 108-1256 | 126 | MG | 108-1188 |
| 60 | M | 109-1256 | 127 | M | 109-1188 |
| 61 | MG | 109-1256 | 128 | MG | 109-1188 |
| 62 | M | 110-1256 | 129 | M | 110-1188 |
| 63 | MG | 110-1256 | 130 | MG | 110-1188 |
| 64 | M | 111-1256 | 131 | M | 111-1188 |
| 65 | MG | 111-1256 | 132 | MG | 111-1188 |
| 66 | M | 112-1356 | 133 | M | 112-1356 |
| 67 | M | 113-1256 | 134 | M | 113-1188 |

Nucleic acids encoding the toxins described in Table 3 are designed in accordance with the general principles for synthetic genes intended for expression in plants, as discussed above.

EXAMPLE 3

Design of a Plant-Optimized Version of the Coding Sequence for the DIG-3 B.t. Insecticidal Protein A DNA sequence having a plant codon bias was designed and synthesized to produce the DIG-3 protein in transgenic monocot and dicot plants. A codon usage table for maize (*Zea mays* L.) was calculated from 706 protein coding sequences (CDs) obtained from sequences deposited in GenBank. Codon usage tables for tobacco (*Nicotiana tabacum*, 1268 CDs), canola (*Brassica napus*, 530 CDs), cotton (*Gossypium hirsutum*, 197 CDs), and soybean (*Glycine max*; ca. 1000 CDs) were downloaded from data at the website http://www.kazusa.or.jp/codon/. A biased codon set that comprises highly used codons common to both maize and dicot datasets, in appropriate weighted average relative amounts, was calculated after omitting any redundant codon used less than about 10% of total codon uses for that amino acid in either plant type. To derive a plant optimized sequence encoding the DIG-3 protein, codon substitutions to the experimentally determined DIG-3 DNA sequence were made such that the resulting DNA sequence had the overall codon composition of the plant-optimized codon bias table. Further refinements of the sequence were made to eliminate undesirable restriction enzyme recognition sites, potential plant intron splice sites, long runs of A/T or C/G residues, and other motifs that might interfere with RNA stability, transcription, or translation of the coding region in plant cells. Other changes were made to introduce desired restriction enzyme recognition sites, and to eliminate long internal Open Reading Frames (frames other than +1). These changes were all made within the constraints of retaining the plant-biased codon composition. Synthesis of the designed sequence was performed by a commercial vendor (DNA2.0, Menlo Park, Calif.).

Additional guidance regarding the production of synthetic genes can be found in, for example, WO 97/13402 and U.S. Pat. No. 5,380,831.

A plant-optimized DNA sequence encoding the full length DIG-3 toxin is given in SEQ ID NO:3. A dicot-optimized DNA sequence encoding the Cry1Ab protoxin segment is disclosed as SEQ ID NO:6. A maize-optimized DNA sequence encoding the Cry1Ab protoxin segment is disclosed as SEQ ID NO:7.

EXAMPLE 4

Construction of Expression Plasmids Encoding DIG-3 Insecticidal Toxin and Expression in Bacterial Hosts Standard cloning methods were used in the construction of *Pseudomonas fluorescens* (Pf) expression plasmids engineered to produce full-length DIG-3 proteins encoded by plant-optimized coding regions. Restriction endonucleases were obtained from New England BioLabs (NEB; Ipswich, Mass.) and T4 DNA Ligase (Invitrogen) was used for DNA ligation. Plasmid preparations were performed using the NucleoBond® Xtra Kit (Macherey-Nagel Inc, Bethlehem, Pa.) or the Plasmid Midi Kit® (Qiagen), following the instructions of the suppliers. DNA fragments were purified using the Millipore Ultrafree®-DA cartridge (Billerica, Mass.) after agarose Tris-acetate gel electrophoresis.

The basic cloning strategy entailed subcloning the DIG-3 toxin coding sequence (CDS) into pDOW1169 at the SpeI and XhoI restriction sites, whereby it is placed under the expression control of the Ptac promoter and the rrnBT1T2 terminator from plasmid pKK223-3 (PL Pharmacia, Milwaukee, Wis.). pDOW1169 is a medium copy plasmid with the RSF1010 origin of replication, a pyrF gene, and a ribosome binding site preceding the restriction enzyme recognition sites into which DNA fragments containing protein coding regions may be introduced, (US Application 20080193974). The expression plasmid, designated pDAB4171, was transformed by electroporation into DC454 (a near wild-type *P. fluorescens* strain having mutations ΔpyrF and lsc::lacI$^{Q1}$), or its derivatives, recovered in SOC-Soy hydrolysate medium, and plated on selective medium (M9 glucose agar lacking uracil, Sambrook et al., supra). Details of the microbiological manipulations are available in Squires et al., (2004), US Patent Application 20060008877, US Patent Application 20080193974, and US Patent Application 20080058262, incorporated herein by reference. Colonies were first screened by PCR and positive clones were then analyzed by restriction digestion of miniprep plasmid DNA. Plasmid DNA of selected clones containing inserts was sequenced, either by using Big Dye® Terminator version 3.1 as recommended by the supplier (Applied Biosystems/Invitrogen), or by contract with a commercial sequencing vendor (MWG Biotech, Huntsville, Ala.). Sequence data were assembled and analyzed using the Sequencher™ software (Gene Codes Corp., Ann Arbor, Mich.).

Growth and Expression Analysis in Shake Flasks. Production of DIG-3 toxin for characterization and insect bioassay was accomplished by shake-flask-grown *P. fluorescens* strains harboring expression constructs (e.g. clone DP2826). Seed cultures grown in M9 medium supplemented with 1% glucose and trace elements were used to inoculate 50 mL of defined minimal medium with 5% glycerol (Teknova Catalog No. 3D7426, Hollister, Calif.). Expression of the DIG-3 toxin gene via the Ptac promoter was induced by addition of isopropyl-β-D-1-thiogalactopyranoside (IPTG) after an initial incubation of 24 hours at 30° with shaking. Cultures were sampled at the time of induction and at various times post-induction. Cell density was measured by optical density at 600 nm ($OD_{600}$). Other culture media suitable for growth of *Pseudomonas fluorescens* may also be utilized, for example, as described in Huang et al. (2007) and US Patent Application 20060008877.

Cell Fractionation and SDS-PAGE Analysis of Shake Flask Samples. At each sampling time, the cell density of samples was adjusted to $OD_{600}$=20 and 1 mL aliquots were centrifuged at 14000×g for five minutes. The cell pellets were frozen at −80°. Soluble and insoluble fractions from frozen shake flask cell pellet samples were generated using EasyLyse™ Bacterial Protein Extraction Solution (EPICENTRE® Biotechnologies, Madison, Wis.). Each cell pellet was resuspended in 1 mL EasyLyse™ solution and further diluted 1:4 in lysis buffer and incubated with shaking at room temperature for 30 minutes. The lysate was centrifuged at 14,000 rpm for 20 minutes at 4° and the supernatant was recovered as the soluble fraction. The pellet (insoluble fraction) was then resuspended in an equal volume of phosphate buffered saline (PBS; 11.9 mM $Na_2HPO_4$, 137 mM NaCl, 2.7 mM KCl, pH7.4).

Samples were mixed 1:1 with 2× Laemmli sample buffer containing β-mercaptoethanol (Sambrook et al., supra.) and boiled for 5 minutes prior to loading onto Criterion XT® Bis-Tris 12% gels (Bio-Rad Inc., Hercules, Calif.) Electrophoresis was performed in the recommended XT MOPS buffer. Gels were stained with Bio-Safe Coomassie Stain according to the manufacturer's (Bio-Rad) protocol and imaged using the Alpha Innotech Imaging system (San Leandro, Calif.).

Inclusion body preparation. Cry protein inclusion body (IB) preparations were performed on cells from *P. fluorescens* fermentations that produced insoluble B.t. insecticidal protein, as demonstrated by SDS-PAGE and MALDI-MS (Matrix Assisted Laser Desorption/Ionization Mass Spectrometry). *P. fluorescens* fermentation pellets were thawed in a 37° water bath. The cells were resuspended to 25% w/v in lysis buffer (50 mM Tris, pH 7.5, 200 mM NaCl, 20 mM EDTA disodium salt (Ethylenediaminetetraacetic acid), 1% Triton X-100, and 5 mM Dithiothreitol (DTT); 5 mL/L of bacterial protease inhibitor cocktail (*P*8465 Sigma-Aldrich, St. Louis, Mo.) were added just prior to use). The cells were suspended using a hand-held homogenizer at lowest setting (Tissue Tearor, BioSpec Products, Inc., Bartlesville, Okla.). Lysozyme (25 mg of Sigma L7651, from chicken egg white) was added to the cell suspension by mixing with a metal spatula, and the suspension was incubated at room temperature for one hour. The suspension was cooled on ice for 15 minutes, then sonicated using a Branson Sonifier 250 (two 1-minute sessions, at 50% duty cycle, 30% output). Cell lysis was checked by microscopy. An additional 25 mg of lysozyme were added if necessary, and the incubation and sonication were repeated. When cell lysis was confirmed via microscopy, the lysate was centrifuged at 11,500×g for 25 minutes (4°) to form the IB pellet, and the supernatant was discarded. The IB pellet was resuspended with 100 mL lysis buffer, homogenized with the hand-held mixer and centrifuged as above. The IB pellet was repeatedly washed by resuspension (in 50 mL lysis buffer), homogenization, sonication, and centrifugation until the supernatant became colorless and the IB pellet became firm and off-white in color. For the final wash, the IB pellet was resuspended in sterile-filtered (0.22 μm) distilled water containing 2 mM EDTA, and centrifuged. The final pellet was resuspended in sterile-filtered distilled water containing 2 mM EDTA, and stored in 1 mL aliquots at −80°.

SDS-PAGE analysis and quantitation of protein in IB preparations was done by thawing a 1 mL aliquot of IB pellet and diluting 1:20 with sterile-filtered distilled water. The diluted sample was then boiled with 4× reducing sample buffer [250 mM Tris, pH6.8, 40% glycerol (v/v), 0.4% Bromophenol Blue (w/v), 8% SDS (w/v) and 8% 13-Mercaptoethanol (v/v)] and loaded onto a Novex® 4-20% Tris-Glycine, 12+2 well gel (Invitrogen) run with 1× Tris/Glycine/SDS buffer (BioRad). The gel was run for 60 min *at* 200 volts then stained with Coomassie Blue (50% G-250/50% R-250 in 45% methanol, 10% acetic acid), and destained with 7% acetic acid, 5% methanol in distilled water. Quantification of target bands was done by comparing densitometric values for the bands against Bovine Serum Albumin (BSA) samples run on the same gel to generate a standard curve.

Solubilization of Inclusion Bodies. Six mL of inclusion body suspension from Pf clone DP2826 (containing 32 mg/mL of DIG-3 protein) were centrifuged on the highest setting of an Eppendorf model 5415C microfuge (approximately 14,000×g) to pellet the inclusions. The storage buffer supernatant was removed and replaced with 25 mL of 100 mM sodium carbonate buffer, pH11, in a 50 mL conical tube. Inclusions were resuspended using a pipette and vortexed to mix thoroughly. The tube was placed on a gently rocking platform at 4° overnight to extract the target protein. The extract was centrifuged at 30,000×g for 30 min at 4°, and the resulting supernatant was concentrated 5-fold using an Amicon Ultra-15 regenerated cellulose centrifugal filter device (30,000 Molecular Weight Cutoff; Millipore). The sample buffer was then changed to 10 mM CAPS [3-(cyclohexamino)1-propanesulfonic acid] pH 10, using disposable PD-10 columns (GE Healthcare, Piscataway, N.J.).

Gel electrophoresis. The concentrated extract was prepared for electrophoresis by diluting 1:50 in NuPAGE® LDS sample buffer (Invitrogen) containing 5 mM dithiothreitol as a reducing agent and heated at 95° for 4 minutes. The sample was loaded in duplicate lanes of a 4-12% NuPAGE® gel alongside five BSA standards ranging from 0.2 to 2 µg/lane (for standard curve generation). Voltage was applied at 200V using MOPS SDS running buffer (Invitrogen) until the tracking dye reached the bottom of the gel. The gel was stained with 0.2% Coomassie Blue G-250 in 45% methanol, 10% acetic acid, and destained, first briefly with 45% methanol, 10% acetic acid, and then at length with 7% acetic acid, 5% methanol until the background cleared. Following destaining, the gel was scanned with a Biorad Fluor-S MultiImager. The instrument's Quantity One v.4.5.2 Software was used to obtain background-subtracted volumes of the stained protein bands and to generate the BSA standard curve that was used to calculate the concentration of DIG-3 protein in the stock solution.

EXAMPLE 5

Insecticidal Activity of Modified DIG-3 Protein Produced in *Pseudomonas fluorescens*

DIG-3 B.t. insecticidal toxin was demonstrated to be active on Lepidopteran species including the European corn borer (ECB; *Ostrinia nubilalis* (Hübner)), cry1F-resistant ECB (rECB), diamondback moth (DBM; *Plutella xylostella* (Linnaeus)), cry1A-resistant DBM (rDBM), corn earworm (CEW; *Helicoverpa zea* (Boddie)), black cutworm (BCW; *Agrotis ipsilon* (Hufnagel)), tobacco budworm (TBW; *Heliothis virescens* (Fabricius)), and cabbage looper (CL; *Trichoplusia ni* (Hübner)). DIG-3 protein was also tested for activity on fall armyworm (FAW, *Spodoptera frugiperda*), Cry1F-resistant FAW (rFAW) and western corn rootworm (WCR, *Diabrotica virgifera virgifera* LeConte).

Sample preparation and bioassays. Inclusion body preparations in 10 mM CAPS pH10 were diluted appropriately in 10 mM CAPS pH 10, and all bioassays contained a control treatment consisting of this buffer, which served as a background check for mortality or growth inhibition.

Protein concentrations in bioassay buffer were estimated by gel electrophoresis using BSA to create a standard curve for gel densitometry, which was measured using a BioRad imaging system (Fluor-S MultiImager with Quantity One software version 4.5.2). Proteins in the gel matrix were stained with Coomassie Blue-based stain and destained before reading.

Purified proteins were tested for insecticidal activity in bioassays conducted with neonate Lepidopteran larvae on artificial insect diet. Larvae of BCW, CEW, CL, DBM, rDBM, ECB, FAW and TBW were hatched from eggs obtained from a colony maintained by a commercial insectary (Benzon Research Inc., Carlisle, Pa.). WCR eggs were obtained from Crop Characteristics, Inc. (Farmington, Minn.). Larvae of rECB and rFAW were hatched from eggs harvested from proprietary colonies (Dow AgroSciences LLC, Indianapolis, Ind.).

The bioassays were conducted in 128-well plastic trays specifically designed for insect bioassays (C-D International, Pitman, N.J.). Each well contained 1.0 mL of Multi-species *Lepidoptera* diet (Southland Products, Lake Village, Ariz.). A 40 µL aliquot of protein sample was delivered by pipette onto the 1.5 cm² diet surface of each well (26.7 µL/cm²). Diet concentrations were calculated as the amount (ng) of DIG-3 protein per square centimeter (cm²) of surface area in the well. The treated trays were held in a fume hood until the liquid on the diet surface had evaporated or was absorbed into the diet.

Within a few hours of eclosion, individual larvae were picked up with a moistened camel hair brush and deposited on the treated diet, one larva per well. The infested wells were then sealed with adhesive sheets of clear plastic, vented to allow gas exchange (C-D International, Pitman, N.J.). Bioassay trays were held under controlled environmental conditions (28° C., ~40% Relative Humidity, 16:8 [Light:Dark]) for 5 days, after which the total number of insects exposed to each protein sample, the number of dead insects, and the weight of surviving insects were recorded. Percent mortality and percent growth inhibition were calculated for each treatment. Growth inhibition (GI) was calculated as follows:

$$GI=[1-(TWIT/TNIT)/(TWIBC/TNIBC)]$$

where TWIT is the Total Weight of Insects in the Treatment,

TNIT is the Total Number of Insects in the Treatment

TWIBC is the Total Weight of Insects in the Background Check (Buffer control), and TNIBC is the Total Number of Insects in the Background Check (Buffer control).

The $GI_{50}$ was determined to be the concentration of DIG-3 protein in the diet at which the GI value was 50%. The $LC_{50}$ (50% Lethal Concentration) was recorded as the concentration of DIG-3 protein in the diet at which 50% of test insects were killed. Statistical analysis (One-way ANOVA) was done using JMP software (SAS, Cary, N.C.)

Table 6 presents the results of bioassay tests of DIG-3 protein on European corn borer and cry1F-resistant European corn borer (rECB). An unexpected and surprising finding is that the rECB test insects were as susceptible to the action of DIG-3 protein as were the wild type ECB insects.

TABLE 6

$LC_{50}$ and $GI_{50}$ values calculated for ECB and rECB, with Confidence Intervals (CI) of 95%

| Insect | $LC_{50}$ (ng/cm²) | 95% CI | $GI_{50}$ (ng/cm²) | 95% CI |
|---|---|---|---|---|
| ECB | 591.9 | 308.1-1315.3 | 122.6 | 45.6-328.4 |
| rECB | 953.6 | 534.1-1953.6 | 270.9 | 53.0-1382.2 |

Table 7 presents the results of bioassays on a broad spectrum of Lepidopteran and a Coleopteran pest (WCR). The DIG-3 protein has unexpected and surprising activity on diamondback moth as well as rDBM. Further the DIG-3 Cry protein is effective in controlling the growth of several other Lepidopteran insects.

TABLE 7

Insecticidal and growth inhibitory effects of DIG-3 protein ingested by test insects

| Test Insect | Response at 9000 ng/cm² | Statistical Analysis* |
|---|---|---|
| DBM | 100% mortality | |
| rDBM | 100% mortality | |
| CL | 75% mortality, significant GI | (GI) P < 0.001, df = 1, α = 0.05 |
| CEW | Significant GI | (GI) P = 0.02, df = 1, α = 0.05 |
| TBW | Visible GI, some mortality | Not available |
| BCW | Visible GI | Not available |
| FAW | No activity observed | |
| rFAW | No activity observed | |
| WCR | No activity observed | |

*GI = Growth Inhibition. P-value = test statistic. df = Degrees of Freedom, α(alpha) level 0.05 = the level of test significance.

EXAMPLE 6

Agrobacterium Transformation

Standard cloning methods are used in the construction of binary plant transformation and expression plasmids. Restriction endonucleases and T4 DNA Ligase are obtained from NEB. Plasmid preparations are performed using the NucleoSpin® Plasmid Preparation kit or the NucleoBond® AX Xtra Midi kit (both from Macherey-Nagel), following the instructions of the manufacturers. DNA fragments are purified using the QIAquick® PCR Purification Kit or the QIAEX II® Gel Extraction Kit (both from Qiagen) after gel isolation.

DNA fragments comprising nucleotide sequences that encode the DIG-3 protein in native or modified forms, or fragments thereof, may be synthesized by a commercial vendor (e.g. DNA2.0, Menlo Park, Calif.) and supplied as cloned fragments in standard plasmid vectors, or may be obtained by standard molecular biology manipulation of other constructs containing appropriate nucleotide sequences. Unique restriction sites internal to a DIG-3 coding region may be identified and DNA fragments comprising the sequences between the restriction sites of the DIG-3 coding region may be synthesized, each such fragment encoding a specific deletion, insertion or other DIG-3 variation. The DNA fragments encoding the modified DIG-3 fragments may be joined to other DIG-3 coding region fragments or other Cry coding region fragments at appropriate restriction sites to obtain a coding region encoding the desired full-length DIG-3 protein, deleted or variant DIG-3 protein, or fused protein. For example, one may identify an appropriate restriction recognition site at the start of a first DIG-3 coding region, and a second restriction site internal to the DIG-3 coding region. Cleavage of this first DIG-3 coding region at these restriction sites would generate a DNA fragment comprising part of the first DIG-3 coding region. A second DNA fragment flanked by analogously-situated compatible restriction sites specific for another DIG-3 coding region or other Cry coding region may be used in combination with the first DNA restriction fragment to construct a variant or fused clone.

In a non-limiting example, a basic cloning strategy may be to subclone full length or modified DIG-3 coding sequences (CDS) into a plant expression plasmid at NcoI and SacI restriction sites. The resulting plant expression cassettes containing the appropriate DIG-3 coding region under the control of plant expression elements, (e.g., plant expressible promoters, 3' terminal transcription termination and polyadenylate addition determinants, and the like) are subcloned into a binary vector plasmid, utilizing, for example, Gateway® technology or standard restriction enzyme fragment cloning procedures. LR Clonase™ (Invitrogen) for example, may be used to recombine the full length and modified gene plant expression cassettes into a binary plant transformation plasmid if the Gateway® technology is utilized. It is convenient to employ a binary plant transformation vector that harbors a bacterial gene that confers resistance to the antibiotic spectinomycin when the plasmid is present in E. coli and Agrobacterium cells. It is also convenient to employ a binary vector plasmid that contains a plant-expressible selectable marker gene that is functional in the desired host plants. Examples of plant-expressible selectable marker genes include but are not limited those that encode the aminoglycoside phosphotransferase gene (aphII) of transposon Tn5, which confers resistance to the antibiotics kanamycin, neomycin and G418, as well as those genes which code for resistance or tolerance to glyphosate; hygromycin; methotrexate; phosphinothricin (bialaphos), imidazolinones, sulfonylureas and triazolopyrimidine herbicides, such as chlorosulfuron, bromoxynil, dalapon and the like.

Electro-competent cells of Agrobacterium tumefaciens strain Z707S (a streptomycin-resistant derivative of Z707; Hepburn et al., 1985) are prepared and transformed using electroporation (Weigel and Glazebrook, 2002). After electroporation, 1 mL of YEP broth (gm/L: yeast extract, 10; peptone, 10; NaCl, 5) are added to the cuvette and the cell-YEP suspension is transferred to a 15 mL culture tube for incubation at 28° in a water bath with constant agitation for 4 hours. The cells are plated on YEP plus agar (25 gm/L) with spectinomycin (200 µg/mL) and streptomycin (250 µg/mL) and the plates are incubated for 2-4 days at 28°. Well separated single colonies are selected and streaked onto fresh YEP+agar plates with spectinomycin and streptomycin as before, and incubated at 28° for 1-3 days.

The presence of the DIG-3 gene insert in the binary plant transformation vector is performed by PCR analysis using vector-specific primers with template plasmid DNA prepared from selected Agrobacterium colonies. The cell pellet from a 4 mL aliquot of a 15 mL overnight culture grown in YEP with spectinomycin and streptomycin as before is extracted using Qiagen Spin® Mini Preps, performed per manufacturer's instructions. Plasmid DNA from the binary vector used in the Agrobacterium electroporation transformation is included as a control. The PCR reaction is completed using Taq DNA polymerase from Invitrogen per manufacture's instructions at 0.5× concentrations. PCR reactions are carried out in a MJ Research Peltier Thermal Cycler programmed with the following conditions: Step 1) 94° for 3 minutes; Step 2) 94° for 45 seconds; Step 3) 55° for 30 seconds; Step 4) 72° for 1 minute per kb of expected product length; Step 5) 29 times to Step 2; Step 6) 72° for 10 minutes. The reaction is maintained at 4° after cycling. The amplification products are analyzed by agarose gel electrophoresis (e.g. 0.7% to 1% agarose, w/v) and visualized by ethidium bromide staining. A colony is selected whose PCR product is identical to the plasmid control.

Alternatively, the plasmid structure of the binary plant transformation vector containing the DIG-3 gene insert is performed by restriction digest fingerprint mapping of plasmid DNA prepared from candidate Agrobacterium isolates by standard molecular biology methods well known to those skilled in the art of Agrobacterium manipulation.

Those skilled in the art of obtaining transformed plants via Agrobacterium-mediated transformation methods will understand that other *Agrobacterium* strains besides Z7075 may be used to advantage, and the choice of strain may depend upon the identity of the host plant species to be transformed.

EXAMPLE 7

Production of DIG-3 B.t. Insecticidal Proteins and Variants in Dicot Plants

*Arabidopsis* Transformation. *Arabidopsis thaliana* Col-01 is transformed using the floral dip method (Weigel and Glazebrook, 2002). The selected *Agrobacterium* colony is used to inoculate 1 mL to 15 mL cultures of YEP broth containing appropriate antibiotics for selection. The culture is incubated overnight at 28° with constant agitation at 220 rpm. Each culture is used to inoculate two 500 mL cultures of YEP broth containing appropriate antibiotics for selection and the new cultures are incubated overnight at 28° with constant agitation. The cells are pelleted at approximately 8700×g for 10 minutes at room temperature, and the resulting supernatant is discarded. The cell pellet is gently resuspended in 500 mL of infiltration media containing: ½× Murashige and Skoog salts (Sigma-Aldrich)/Gamborg's B5 vitamins (Gold BioTechnology, St. Louis, Mo.), 10% (w/v) sucrose, 0.044 µM benzylaminopurine (10 µL/liter of 1 mg/mL stock in DMSO) and 300 µL/liter Silwet L-77. Plants approximately 1 month old are dipped into the media for 15 seconds, with care taken to assure submergence of the newest inflorescence. The plants are then laid on their sides and covered (transparent or opaque) for 24 hours, washed with water, and placed upright. The plants are grown at 22°, with a 16-hour light/8-hour dark photoperiod. Approximately 4 weeks after dipping, the seeds are harvested.

Arabidopsis Growth and Selection. Freshly harvested T1 seed is allowed to dry for at least 7 days at room temperature in the presence of desiccant. Seed is suspended in a 0.1% agar/water (Sigma-Aldrich) solution and then stratified at 4° for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) is covered with fine vermiculite, sub-irrigated with Hoagland's solution (Hoagland and Arnon, 1950) until wet, then allowed to drain for 24 hours. Stratified seed is sown onto the vermiculite and covered with humidity domes (KORD Products, Bramalea, Ontario, Canada) for 7 days. Seeds are germinated and plants are grown in a Conviron (Models CMP4030 or CMP3244; Controlled Environments Limited, Winnipeg, Manitoba, Canada) under long day conditions (16 hours light/8 hours dark) at a light intensity of 120-150 µmmol/m² sec under constant temperature (22°) and humidity (40-50%). Plants are initially watered with Hoagland's solution and subsequently with deionized water to keep the soil moist but not wet.

The domes are removed 5-6 days post sowing and plants are sprayed with a chemical selection agent to kill plants germinated from nontransformed seeds. For example, if the plant expressible selectable marker gene provided by the binary plant transformation vector is a pat or bar gene (Wehrmann et al., 1996), transformed plants may be selected by spraying with a 1000× solution of Finale (5.78% glufosinate ammonium, Farnam Companies Inc., Phoenix, Ariz.). Two subsequent sprays are performed at 5-7 day intervals. Survivors (plants actively growing) are identified 7-10 days after the final spraying and transplanted into pots prepared with Sunshine Mix LP5. Transplanted plants are covered with a humidity dome for 3-4 days and placed in a Conviron under the above-mentioned growth conditions.

Those skilled in the art of dicot plant transformation will understand that other methods of selection of transformed plants are available when other plant expressible selectable marker genes (e.g. herbicide tolerance genes) are used.

Insect Bioassays of transgenic Arabidopsis. Transgenic Arabidopsis lines expressing modified Cry proteins are demonstrated to be active against sensitive insect species in artificial diet overlay assays. Protein extracted from transgenic and non-transgenic Arabidopsis lines is quantified by appropriate methods and sample volumes are adjusted to normalize protein concentration. Bioassays are conducted on artificial diet as described above. Non-transgenic *Arabidopsis* and/or buffer and water are included in assays as background check treatments.

EXAMPLE 8

*Agrobacterium* Transformation for Generation of Superbinary Vectors

The *Agrobacterium* superbinary system is conveniently used for transformation of monocot plant hosts. Methodologies for constructing and validating superbinary vectors are well disclosed and incorporated herein by reference (Operating Manual for Plasmid pSB1, Version 3.1, available from Japan Tobacco, Inc., Tokyo, Japan). Standard molecular biological and microbiological methods are used to generate superbinary plasmids. Verification/validation of the structure of the superbinary plasmid is done using methodologies as described above for binary vectors, and may be modified as suggested in the Operating Manual for Plasmid pSB1.

EXAMPLE 9

Production of DIG-3 B.t. Insecticidal Proteins and Variants in Monocot Plants Agrobacterium-Mediated Transformation of Maize. Seeds from a High II $F_1$ cross (Armstrong et al., 1991) are planted into 5-gallon-pots containing a mixture of 95% Metro-Mix 360 soilless growing medium (Sun Gro Horticulture, Bellevue, Wash.) and 5% clay/loam soil. The plants are grown in a greenhouse using a combination of high pressure sodium and metal halide lamps with a 16:8 hour Light:Dark photoperiod. For obtaining immature $F_2$ embryos for transformation, controlled sib-pollinations are performed. Immature embryos are isolated at 8-10 days post-pollination when embryos are approximately 1.0 to 2.0 mm in size.

Infection and co-cultivation. Maize ears are surface sterilized by scrubbing with liquid soap, immersing in 70% ethanol for 2 minutes, and then immersing in 20% commercial bleach (0.1% sodium hypochlorite) for 30 minutes before being rinsed with sterile water. A suspension of *Agrobacterium* cells containing a superbinary vector is prepared by transferring 1-2 loops of bacteria grown on YEP solid medium containing 100 mg/L spectinomycin, 10 mg/L tetracycline, and 250 mg/L streptomycin at 28° for 2-3 days into 5 mL of liquid infection medium (LS Basal Medium (Linsmaier and Skoog, 1965), N6 vitamins (Chu et al., 1975), 1.5 mg/L 2,4-Dichlorophenoxyacetic acid (2,4-D), 68.5 gm/L sucrose, 36.0 gm/L glucose, 6 mM L-proline, pH 5.2) containing 100 μM acetosyringone. The solution was vortexed until a uniform suspension was achieved, and the concentration is adjusted to a final density of about 200 Klett units, using a Klett-Summerson colorimeter with a purple filter, or an optical density of approximately 0.4 *at* 550 nm. Immature embryos are isolated directly into a micro centrifuge tube containing 2 mL of the infection medium. The medium is removed and replaced with 1 mL of the *Agrobacterium* solution with a density of 200 Klett units, and the *Agrobacterium* and embryo solution is incubated for 5 minutes at room temperature and then transferred to co-cultivation medium (LS Basal Medium, N6 vitamins, 1.5 mg/L 2,4-D, 30.0 gm/L sucrose, 6 mM L-proline, 0.85 mg/L $AgNO_3$, 100 μM acetosyringone, 3.0 gm/L Gellan gum (PhytoTechnology Laboratories., Lenexa, Kans.), pH 5.8) for 5 days at 25° under dark conditions.

After co-cultivation, the embryos are transferred to selective medium after which transformed isolates are obtained over the course of approximately 8 weeks. For selection of maize tissues transformed with a superbinary plasmid containing a plant expressible pat or bar selectable marker gene, an LS based medium (LS Basal medium, N6 vitamins, 1.5 mg/L 2,4-D, 0.5 gm/L MES (2-(N-morpholino)ethanesulfonic acid monohydrate; PhytoTechnologies Labr.), 30.0 gm/L sucrose, 6 mM L-proline, 1.0 mg/L $AgNO_3$, 250 mg/L cefotaxime, 2.5 gm/L Gellan gum, pH 5.7) is used with Bialaphos (Gold BioTechnology). The embryos are transferred to selection media containing 3 mg/L Bialaphos until embryogenic isolates were obtained. Recovered isolates are bulked up by transferring to fresh selection medium at 2-week intervals for regeneration and further analysis.

Those skilled in the art of maize transformation will understand that other methods of selection of transformed plants are available when other plant expressible selectable marker genes (e.g. herbicide tolerance genes) are used.

Regeneration and seed production. For regeneration, the cultures are transferred to "28" induction medium (MS salts and vitamins, 30 gm/L sucrose, 5 mg/L Benzylaminopurine, 0.25 mg/L 2,4-D, 3 mg/L Bialaphos, 250 mg/L cefotaxime, 2.5 gm/L Gellan gum, pH 5.7) for 1 week under low-light conditions (14 $\mu Em^{-2}s^{-1}$) then 1 week under high-light conditions (approximately 89 $\mu Em^{-2}s^{-1}$). Tissues are subsequently transferred to "36" regeneration medium (same as induction medium except lacking plant growth regulators). When plantlets grow to 3- 5cm in length, they were transferred to glass culture tubes containing SHGA medium (Schenk and Hildebrandt salts and vitamins (1972); Phyto-Technologies Labr.), 1.0 gm/L myo-inositol, 10 gm/L sucrose and 2.0 gm/L Gellan gum, pH 5.8) to allow for further growth and development of the shoot and roots. Plants are transplanted to the same soil mixture as described earlier herein and grown to flowering in the greenhouse. Controlled pollinations for seed production are conducted.

EXAMPLE 10

Bioassay of Transgenic Maize

Bioactivity of the DIG-3 protein and variants produced in plant cells is demonstrated by conventional bioassay methods (see, for example Huang et al., 2006). One is able to demonstrate efficacy, for example, by feeding various plant tissues or tissue pieces derived from a plant producing a DIG-3 toxin to target insects in a controlled feeding environment. Alternatively, protein extracts may be prepared from various plant tissues derived from a plant producing the DIG-3 toxin and incorporate the extracted proteins in an artificial diet bioassay as previously described herein. It is to be understood that the results of such feeding assays are to be compared to similarly conducted bioassays that employ appropriate control tissues from host plants that do not produce the DIG-3 protein or variants, or to other control samples.

References

An, G., Watson, B. D., Stachel, S., Gordon, M. P., Nester, E. W. (1985) New cloning vehicles for transformation of higher plants. EMBO J. 4:277-284.

Altschul, S. F., Gish, W., Miller, W., Myers, E. W., Lipman, D. J. (1990) Basic local alignment search tool. J. Mol. Biol. 215:403-410.

Altschul, S. F., Madden, T. L., Schäffer, A. A., Zhang, J., Zhang, Z., Miller, W., Lipman, D. J. (1997) Gapped BLAST and PSI-BLAST: a new generation of protein database search programs. Nucl. Acids Res. 25:3389-3402.

Armstrong, C. L., Green, C. E., Phillips, R. L. (1991) Development and availability of germplasm with high TypeII culture formation response. Maize Genet. Coop. Newslett. 65:92-93.

Aronson, A. I., Han, E.-S., McGaughey, W., Johnson, D. (1991) The solubility of inclusion proteins from *Bacillus thuringiensis* is dependent upon protoxin composition and is a factor in toxicity to insects. Appl. Environ. Microbiol. 57:981-986.

Aronson, A. I., Geng, C., Wu. L. (1999) Aggregation of *Bacillus thuringiensis* Cry1A toxins upon binding to target insect larval midgut vesicles. Appl. Environ. Microbiol. 65:2503-2507.

Arvidson, H., Dunn, P. E., Strand, S., Aronson, A. I. (1989) Specificity of *Bacillus thuringiensis* for lepidopteran larvae: factors involved in vivo and in the structure of a purified toxin. Molec. Microbiol. 3:1533-1543.

Ausubel et al., eds. (1995) *Current Protocols in Molecular Biology*, Chapter 2 (Greene Publishing and Wiley-Interscience, New York).

Bailey, J. M., Shenov, N. R., Ronk, M., and Shively, J. E., (1992) Automated carboxy-terminal sequence analysis of peptides. Protein Sci. 1:68-80.

Beltz, G. A., Jacobs, K. A., Eickbush, T. H., Cherbas, P. T., Kafatos, F. C. (1983) Isolation of multigene families and determination of homologies by filter hybridization methods. In Wu, R., Grossman, L., Moldave, K. (eds.) Methods of Enzymology, Vol. 100 Academic Press, New York pp. 266-285.

Bown, D. P., Wilkinson, H. S., Jongsma, M. A., Gatehouse, J. A. (2004) Characterisation of cysteine proteinases responsible for digestive proteolysis in guts of larval western corn rootworm (*Diabrotica virgifera*) by expression in the yeast *Pichia pastoris*. Insect Biochem. Molec. Biol. 34: 305-320.

Bravo, A., Gill, S. S., Soberon, M. (2007) Mode of action of *Bacillus thuringiensis* Cry and Cyt toxins and their potential for insect control. Toxicon 49:423-435.

Caruthers, M. H., Kierzek, R., Tang, J. Y. (1987) Synthesis of oligonucleotides using the phosphoramidite method. Bioactive Molecules (Biophosphates Their Analogues) 3:3-21.

Christeller, J. T., Laing, W. A., Markwick, N. P., Burgess, E. P. J. (1992) Midgut protease activities in 12 phytophagous lepidopteran larvae: dietary and protease inhibitor interactions. Insect Biochem. Molec. Biol. 22:735-746.

Chu, C. C., Wand, C. C., Sun, C. S., Hsu, C., Yin, K. C., Chu, C. Y., Bi, F. Y. (1975) Establishment of an efficient medium for anther culture of rice through comparative experiments on the nitrogen sources. Scientia Sinica 18:659-668.

Crameri, A., Cwirla, S., Stemmer, W. P. C. (1996a) Construction and evolution of antibody-phage libraries by DNA shuffling. Nat. Med. 2:100-103.

Crameri, A., Dawes, G., Rodriguez, E., Silver, S., Stemmer, W. P. C. (1997) Molecular evolution of an arsenate detoxification pathway by DNA shuffling. Nat. Biotech. 15:436-438.

Crameri, A., Whitehom, E. A., Tate, E., Stemmer, W. P. C. (1996b) Improved green fluorescent protein by molecular evolution using DNA shuffling. Nat. Biotech. 14:315-319.

de Maagd, R. A., Kwa, M. S., van der Klei, H., Yamamoto, T., Schipper, B., Vlak, J. M., Stiekema, W. J., Bosch, D. (1996) Domain III substitution in *Bacillus thuringiensis* delta-endotoxin CryIA(b) results in superior toxicity for *Spodoptera exigua* and altered membrane protein recognition. Appl. Environ. Microbiol. 62:1537-1543.

de Maagd, R. A., Bravo, A., Berry, C., Crickmore, N., Schnepf, E. (2003) Structure, diversity, and evolution of protein toxins from spore-forming entomopathogenic bacteria. Annu. Rev. Genet. 37:409-433.

Diaz-Mendoza, M., Farinos, G. P., Castanera, P., Hernandez-Crespo, P., Ortego, F. (2007) Proteolytic processing of native Cry1Ab toxin by midgut extracts and purified trypsins from the Mediterranean corn borer *Sesamia nonagrioide*. J. Insect Physiol. 53:428-435.

Englemann, F., Geraerts, W. P. M., (1980) The proteases and the protease inhibitor in the midgut of *Leucophaea maderae*. J. Insect Physiol. 261:703-710.

Fraley, R. T., Rogers, S. G., Horsch, R. B. (1986) Genetic transformation in higher plants. Crit. Rev. Plant Sci. 4:1-46.

Gazit, E., La Rocca, P., Sansom, M. S. P., Shai, Y. (1998) The structure and organization within the membrane of the helices composing the pore-forming domain of *Bacillus thuringiensis* delta-endotoxin are consistent with an "umbrella-like" structure of the pore. Proc. Nat. Acad. Sci. USA 95:12289-12294.

Ge, A., Rivers, D., Milne, R., Dean, D. H. (1991) Functional domains of *Bacillus thuringiensis* insecticidal crystal proteins. Refinement of *Heliothis virescens* and *Trichoplusia ni* specificity domains on CryIA(c). J. Biol. Chem. 266: 17954-17958.

Gillikin, J W., Bevilacqua, S., Graham, J. S. (1992) Partial characterization of digestive tract proteinases from western corn rootworm larvae, *Diabrotica virgifera*. Arch. Insect Biochem. Physiol. 19:285-298.

Gomez, I., Sanchez, J., Miranda, R., Bravo, A., Soberon, M. (2002) Cadherin-like receptor binding facilitates proteolytic cleavage of helix alpha-1 in domain I and oligomer pre-pore formation of *Bacillus thuringiensis* Cry1Ab toxin. FEBS Lett. 513:242-246.

Haider, M. Z., Knowles, B. H., Ellar, D. J. (1986) Specificity of *Bacillus thuringiensis* var. *colmeri* insecticidal δ-endotoxin is determined by differential proteolytic processing of the protoxin by larval gut proteases. Eur. J. Biochem. 156:531-540.

Heckel, D. G., Gahan, L. J., Baxter, S. W., Zhao, J-Z., Shelton, A. M., Gould, F., Tabashnik, B. E. (2007) The diversity of Bt resistance genes in species of *Lepidoptera*. J. Invert. Pathol. 95:192-197.

Hepburn, A. G., White, J., Pearson, L., Maunders, M. J., Clarke, L. E., Prescott, A. G. Blundy, K. S. (1985) The use of pNJ5000 as an intermediate vector for the genetic manipulation of *Agrobacterium* Ti-plasmids. J. Gen. Microbiol. 131: 2961-2969.

Hoagland, D. R., Arnon, D. I. (1950) The water-culture method of growing plants without soil. Calif. Agr. Expt. Sta. Circ. 347.

Hofte, H., de Greve, H., Seurinck, J., Jansens, S., Mahillon, J., Ampe, C., Vandekerckhove, J., Vanderbruggen, H., van Montagu, M., Zabeau, M., Vaeck, M. (1986) "Structural and functional analysis of a cloned delta endotoxin of *Bacillus thuringiensis* berliner 1715." Eur. J. Biochem. 161:273-280.

Horton, R. M., Hunt, H. D., Ho, S. N., Pullen, J. K., Pease, L. R. (1989) Engineering hybrid genes without the use of restriction enzymes: gene splicing by overlap extension. Gene 77:61-68.

Huang, F., Rogers, L. B., Rhett, G. H. (2006) Comparative susceptibility of European corn borer, southwestern corn borer, and sugarcane borer (*Lepidoptera*: Crambidae) to Cry1Ab protein in a commercial *Bacillus thuringiensis* corn hybrid. J. Econ. Entomol. 99:194-202.

Huang, K-X., Badger, M., Haney, K., Evans, S. L. (2007) Large scale production of *Bacillus thuringiensis* PS149B1 insecticidal proteins Cry34Ab1 and Cry35Ab1 from *Pseudomonas fluorescens*. Prot. Express. Purific. 53:325-330.

Janmaat, A. F., Myers, A. H. (2003) Rapid evolution and the cost of resistance to *Bacillus thuringiensis* in greenhouse populations of cabbage loopers, *Trichoplusia ni*. Proc. Royal Soc. London. Ser. B, Biolog. Sci. 270:2263-2270.

Janmaat, A. F., Myers, A. H. (2005) The cost of resistance to *Bacillus thuringiensis* varies with the host plant of *Trichoplusia ni*. Proc. Royal Soc. London. Ser. B, Biolog. Sci. 272: 1031-1038.

Karlin, S., Altschul, S. F. (1990) Methods for assessing the statistical significance of molecular sequence features by using general scoring schemes. Proc. Natl. Acad. Sci. USA 87:2264-2268.

Karlin, S., Altschul, S. F. (1993) Applications and statistics for multiple high-scoring segments in molecular sequences. Proc. Natl. Acad. Sci. USA 90:5873-5877.

Keller, G. H., Manak, M. M. (1993) DNA Probes, Background, Applications, Procedures. Stockton Press, New York, N.Y.

Knight, J. S., Broadwell, A. H., Grant, W. N., Shoemaker, C. B. (2004) A Strategy for Shuffling Numerous *Bacillus thuringiensis* Crystal Protein Domains. J. Econ. Entomol. 97:1805-1813.

Koiwa, H., Shade, R. E., Zhu-Salzman, K., D'Urzo, M. P., Murdock, L. L., Bressan, R. A., Hasegawa, P. M. (2000) A plant defensive cystatin (soyacystatin) targets cathepsin L-like digestive cysteine proteinases (DvCALs) in the larval midgut of western corn rootworm *Diabrotica virgifera virgifera*. FEBS Letters 471:67-70.

Larson, S. M., England, J. L., Desjarlais, J. R., Pande, V. S. (2002) Thoroughly sampling sequence space: Large-scale protein design of structural ensembles. Protein Sci. 11:2804-2813.

Lee, L.-Y., Gelvin, S. B. (2008) T-DNA binary vectors and systems. Plant Physiol. 146: 325-332.

Linsmaier, E. M., Skoog, F. (1965) Organic growth factor requirements of tobacco tissue. Physiologia Plantarum 18:100-127.

Littlefield, J. W. (1964) Selection of hybrids from matings of fibroblasts in vitro and their presumed recombinants. Science 145:709-710.

Meinkoth, J., Wahl, G. (1984) Hybridization of nucleic acids immobilized on solid supports. Anal. Biochem. 138: 267-284.

Myers, E., Miller, W. (1988) Optimal alignments in linear space. CABIOS 4:11-17.

Naimov, S., Weemen-Hendriks, M., Dukiandjiev, S., de Maagd, R. A. (2001) *Bacillus thuringiensis* delta-endotoxin Cry1 hybrid proteins with increased activity against the Colorado Potato Beetle. Appl. Environ. Microbiol. 11:5328-5330.

Needleman, S. B., Wunsch, C. D. (1970) A general method applicable to the search for similarities in the amino acid sequence of two proteins. J. Mol. Biol. 48:443-453.

Nunez-Valdez, M.-E., Sanchez, J., Lina, L., Guereca, L., Bravo, A. (2001) Structural and functional studies of alpha-helix 5 region from *Bacillus thuringiensis* Cry1Ab delta-endotoxin. Biochim. Biophys. Acta, Prot. Struc. Molec. Enzymol. 1546:122-131.

Ochoa-Campuzano, C., Real, M. D., Martinez-Ramirez, A. C., Bravo, A., Rausell, C. (2007) An ADAM metalloprotease is a Cry3Aa *Bacillus thuringiensis* toxin receptor. Biochem. Biophys. Res. Commun. 362:437-442.

Pigott, C. R., Ellar, D. J. (2007) Role of receptors in *Bacillus thuringiensis* crystal toxin activity. Microbiol. Molec. Biol. Rev. 71:255-281.

Rang, C., Vachon, V., de Maagd, R. A., Villalon, M., Schwartz, J.-L., Bosch, D., Frutos, R., Laprade R. (1999) Interaction between functional domains of *Bacillus thuringiensis* insecticidal crystal proteins. Appl. Environ. Microbiol. 65:2918-2925.

Sambrook, J., Fritsch, E. F., Maniatis, T. (1989) *Molecular Cloning: A Laboratory Manual* (2nd ed., Cold Spring Harbor Laboratory Press, Plainview, N.Y.)

Schenk, R. U., Hildebrandt, A. C. (1972) Medium and techniques for induction and growth of monocotyledonous and dicotyledonous plant cell cultures. Can. J. Bot. 50:199-204

Schnepf, H. E., Tomczak, K., Ortega, J. P., Whiteley, H. R. (1990) Specificity-determining regions of a Lepidopteran-specific insecticidal protein produced by *Bacillus thuringiensis*. J. Biol. Chem. 265:20923-20930.

Soberon, M., Pardo-Lopez, L., Lopez, I., Gomez, I., Tabashnik, B. E., Bravo, A. (2007) Engineering modified Bt toxins to counter insect resistance. Science 318:1640-1642.

Squires, C. H., Retallack, D. M., Chew, L. C., Ramseier, T. M., Schneider, J. C., Talbot, H. W. (2004) Heterologous protein production in *P. fluorescens*. Bioprocess Intern. 2:54-59.

Stemmer, W. P. C. (1994a) DNA shuffling by random fragmentation and reassembly: in vitro recombination for molecular evolution. Proc. Natl. Acad. Sci. USA 91:10747-10751

Stemmer, W. P. C. (1994b) Rapid evolution of a protein in vitro by DNA shuffling. Nature 370: 389-391.

Stemmer, W. P. C. (1995) Searching sequence space. Bio/Technology 13:549-553.

Stewart, L. (2007) Gene synthesis for protein production. Encylopedia of Life Sciences. John Wiley and Sons, Ltd.

Stewart, L., Burgin, A. B., (2005) Whole gene synthesis: a gene-o-matic future. Frontiers in Drug Design and Discovery 1:297-341.

Suggs, S. V., Miyake, T., Kawashime, E. H., Johnson, M. J., Itakura, K., R. B. Wallace, R. B. (1981) ICN-UCLA Symposium. Dev. Biol. Using Purified Genes, D. D. Brown [ed.], Academic Press, New York, 23:683-69

Tabashnik, B. E., Finson, N., Groeters, F. R., Moar, W. J., Johnson, M. W., Luo, K., Adang, M. J. (1994) Reversal of resistance to *Bacillus thuringiensis* in *Plutella xylostella*. Proc. Nat. Acad. Sci. USA 91:4120-4124.

Tabashnik, B. E., Gassmann, A. J., Crowder, D. W., Carriere, T. (2008) Insect resistance to Bt crops: evidence versus theory. Nat. Biotech. 26:199-202.

Taggart, R. T., Samloff, I. M. (1983) Stable antibody-producing murine hybridomas. Science 219:1228-1230.

Thie, N. M. R., Houseman J. G. (1990) Identification of cathepsin B, D and H in the larval midgut of Colorado potato beetle, *Leptinotarsa decemlineata* say (Coleoptera: Chrysomelidae) Insect Biochem. 20:313-318.

Thompson, J. D., Higgins, D. G., Gibson, T. J. (1994) CLUSTAL W: improving the sensitivity of progressive multiple sequence alignment through sequence weighting, position-specific gap penalties and weight matrix choice. Nucl. Acids Res. 22:4673-4680.

Tijssen, P. (1993) Laboratory Techniques in Biochemistry and Molecular Biology Hybridization with Nucleic Acid Probes, Part I, Chapter 2. P. C. van der Vliet [ed.], (Elsevier, N.Y.)

Varshaysky, A. (1997) The N-end rule pathway of protein degradation. Genes to Cells 2:13-28.

Walters, F. S., Slatin, S. L., Kulesza, C. A., English, L. H. (1993) Ion channel activity of N-terminal fragments from Cry1A(c) delta-endotoxin. Biochem. Biophys. Res. Commun. 196:921-926.

Walters. F. S., Stacy, C. M., Lee, M. K., Palekar, N., Chen, J. S. (2008) An engineered chymotrypsin/cathepsin G site in domain I renders *Bacillus thuringiensis* Cry3A active against western corn rootworm larvae. Appl. Environ. Microbiol. 74:367-374.

Wehrmann, A., Van Vliet, A., Opsomer, C., Botterman, J., Schulz, A. (1996) The similarities of bar and pat gene products make them equally applicable for plant engineers. Nat. Biotechnol. 14:1274-1278.

Weigel, D., Glazebrook, J. [eds.] (2002) *Arabidopsis*: A Laboratory Manual. Cold Spring Harbor Press, Cold Spring Harbor, N.Y., 354 pages.

Witkowski, J. F., Wedberg, J. L., Steffey, K. L., Sloderbeck, P. E., Siegfried, B. D., Rice, M. E., Pilcher, C. D., Onstad, D. W., Mason, C. E., Lewis, L. C., Landis, D. A., Keaster, A. J., Huang, F., Higgins, R. A., Haas, M. J., Gray, M. E., Giles, K. L., Foster, J. E., Davis, P. M., Calvin, D. D., Buschman, L. L., Bolin, P. C., Barry, B. D., Andow, D. A., Alstad, D. N. (2002) Bt corn and European Corn Borer (Ostlie, K. R., Hutchison, W. D., Hellmich, R. L. (eds)). University of Minnesota Extension Service. Publ. WW-07055.

Wolfson, J. L., Murdock, L. L. (1990) Diversity in digestive proteinase activity among insects. J. Chem. Ecol. 16:1089-1102.

Worley, C. K., Ling, R., Callis, J. (1998) Engineering in vivo instability of firefly luciferase and *Escherichia coli* β-glucuronidase in higher plants using recognition elements from the ubiquitin pathway. Plant Molec. Biol. 37:337-347.

---

The invention claimed is:

1. An isolated polypeptide comprising a core toxin segment comprising the amino acid sequence of residues 113 to 643 of SEQ ID NO: 2, wherein said polypeptide has insecticidal activity.

2. An isolated polypeptide comprising a core toxin segment selected from the group consisting of (a) a polypeptide comprising the amino acid sequence of residues 73 to 643 of SEQ ID NO: 2; and (b) a polypeptide comprising an amino acid sequence having at least 97% sequence identity to the amino acid sequence of residues 73 to 643 of SEQ ID NO:2; wherein said polypeptide has insecticidal activity.

3. The isolated polypeptide of claim 2 comprising a core toxin segment selected from the group consisting of (a) a polypeptide comprising the amino acid sequence of residues 1 to 643 of SEQ ID NO: 2; and (b) a polypeptide comprising an amino acid sequence having at least 97% sequence identity to the amino acid sequence of residues 1 to 643 of SEQ ID NO:2; wherein said polypeptide has insecticidal activity.

4. A plant comprising the polypeptide of claim 2.

5. A method for controlling a pest population comprising contacting said population with a pesticidally effective amount of the polypeptide of claim 2.

6. An isolated polynucleotide that encodes the polypeptide of claim 2.

7. The isolated polynucleotide of claim 6 wherein said polynucleotide comprises SEQ ID NO: 1 or SEQ ID NO:3.

8. The polypeptide of claim 2, wherein said polypeptide comprises SEQ ID NO: 2 or SEQ ID NO: 5.

9. A DNA construct comprising the polynucleotide of claim 2 operably linked to a promoter that is not derived from *Bacillus thuringiensis* and is capable of driving expression in a plant.

10. A transgenic plant that comprises the DNA construct of claim 9 stably incorporated into its genome.

11. A method for protecting a plant from a pest comprising introducing into said plant the construct of claim 9.

12. The polypeptide of claim 2 wherein said polypeptide has insecticidal activity against European corn borer.

* * * * *

SEQUENCE LISTING

<160> NUMBER OF SEQ ID NOS: 7

<210> SEQ ID NO 1
<211> LENGTH: 3771
<212> TYPE: DNA
<213> ORGANISM: Bacillus thuringiensis
<220> FEATURE:
<221> NAME/KEY: misc_feature
<222> LOCATION: (1)..(3)
<223> OTHER INFORMATION: translation start codon specifying Met

<400> SEQUENCE: 1

```
ttgacttcaa ataggaaaaa tgagaatgaa attataaatg ctttatcgat tccaacggta      60
tcgaatcctt ccacgcaaat gaatctatca ccagatgctc gtattgaaga tagcttgtgt     120
gtagccgagg tgaacaatat tgatccattt gttagcgcat caacagtcca aacgggtata     180
aacatagctg gtagaatatt gggcgtatta ggtgtgccgt ttgctggaca actagctagt     240
```

```
ttttatagtt ttcttgttgg tgaattatgg cctagtggca gagatccatg ggaaattttc    300
ctggaacatg tagaacaact tataagacaa caagtaacag aaaatactag gaatacggct    360
attgctcgat tagaaggtct aggaagaggc tatagatctt accagcaggc tcttgaaact    420
tggttagata accgaaatga tgcaagatca agaagcatta ttcttgagcg ctatgttgct    480
ttagaacttg acattactac tgctataccg cttttcagaa tacgaaatca agaggttcca    540
ttattaatgg tatatgctca agctgcaaat ttacacctat tattattgag ggacgcatcc    600 cttttggta gtgaatgggg gacggcatct tccgatgtta accaatatta ccaagaacaa    660
atcagatata cagaggaata ttctaaccat tgcgtacaat ggtataatac ggggctaaat    720
aacttaagag ggacaaatgc tgaaagttgg gtacggtata atcaattccg cagagaccta    780
acattagggg tattagatct agtggcccta ttcccaagtt atgacactcg cacttatcca    840
atcaatacga gtgctcagtt aacaagagaa gtttatacag acgcaattgg gaccgtacat    900
ccgagtcaag cttttgcaag tacgacttgg tttaataata atgcaccatc gttttctgcc    960
atagaagctg ccgttatcag gcctccgcat ctacttgatt ttccagaaca acttacaatt   1020
tacagcacat taagtcgatg gagtaacact cagtttatga atatatgggc aggtcataga   1080
cttgaatccc gcccaatagc agggtcatta aatacctcta cacaaggatc taccaatact   1140
tctattaatc ctgtaacatt acagtttacg tctcgagaca tttataggac tgaatcattg   1200
gcagggctaa atatatttat aactcaacct gttaatgggg ttccttgggt tagatttaat   1260
tggagaaatc ccctgaattc tcttagaggt agccttctct atacgatagg gtatactgga   1320
gttgggacgc aattacaaga ttcagaaact gaattacccc cagaaacaac agaacgacca   1380
aattatgaat catatagtca tagattatct catataggac tcatttcatc atctcatgtg   1440
agagcattgg tatattcttg gacgcaccgt agtgcagatc gtacgaatac gattggacca   1500
aatagaatta ctcaaattcc tgcagtgaag ggaagatttc ttttttaatgg ctctgtaatt   1560 tcaggaccag gatttactgg tggagacgta gttagattga ataggaataa tggtaatatt   1620
caaaatagag ggtatattga agttccaatt caattcacgt cgacatctac cagatatcga   1680
gttcgagtac gttatgcttc tgtaacctcg attgagctca atgttaattg gggcaattca   1740
tcaattttta cgaacacatt accagcaaca gctgcatcat tagataatct acaatcaggg   1800
gattttggtt atgttgaaat caacaatgct tttacatccg caacaggtaa tatagtaggt   1860
gttagaaatt ttagtgcaaa tgcagaggta ataatagaca gatttgaatt tatcccagtt   1920
actgcaacct tcgaggcaaa atatgattta gaaagagcac aaaaggcggt gaatgctctg   1980
tttacttcta caaatccaag aagattgaag acagatgtga cagattatca tattgaccaa   2040
gtgtccaatc tggtggtatg tttatcagat gaattttgct tggatgagaa gcagaaatta   2100
tttgagaaag tgaaatatgc gaagcgactc agtgatgaaa gaaacttact ccaagatcca   2160
aacttcacat tcatcaatgg gcaaccaagt tttgcatcca tcgatggaca atcaaacttc   2220
acctctatta atgagctatc taatcatgga tggtggggca gtgcgaatgt taccattcag   2280
gaagggaatg acgtatttaa agagaattac gtcacactac cgggtacttt taatgagtgt   2340
tatccaaatt atttatatca aaaaatagga gagtcagaat taaaggctta tacgcgctat   2400
caattaagag ggtatattga agatagtcaa gatctagaga tttatttaat tcgttacaat   2460
gcaaagcatg aaacattaaa tgttccaggt accgagtccc tatggccgct ttcagttgaa   2520
agcccaatcg gaaggtgcgg agaaccaaat cgatgcgcac cacattttgg atggaatcct   2580
gatctagatt gttcctgcag agatagagaa aaatgtgcgc atcattccca tcatttcact   2640
```

-continued

```
ttggatattg atgttggatg cacagacttg caagaggatc taggcgtgtg ggttgtattc    2700
aagattaaga cgcaggaagg ttatgcaaga ttaggaaatc tggaatttat cgaagagaaa    2760
ccattaattg gagaagcact gtctcgtgtg aagagagcgg aaaaaaaatg gagagacaaa    2820
agggaaaaac tacaagtgga aacaaaacga gtatatatag acgcaaaaga agctgtggat    2880
gctttattcg tagattctca atatgataga ttacaagcag atacaaacat cggtatgatt    2940
catgcggcag atagacttgt tcatcggatc cacgaggctt atcttccaga actacctttc    3000
attccaggaa taaatgtggt gattttttgaa gaattagaaa accgtatttc tactgcattt    3060
tccttatatg atgcgagaaa tgtcattaaa aatggcgatt tcaataatgg attgacatgc    3120
tggaacgtga aagggcatgt agaggtacag cagctgaaca atcatcgttc ggtccttgtc    3180
atcccggaat gggaagcaga gtttcacaa aaggtgcgcg tctgtccagg tcgtggctat    3240
attcttcgtg tcacagcgta caaagaggga tatggggaag gctgcgtaac tattcatgaa    3300
gtcgataata atacagacca attgaagttt agcaactgtg agaaaggaca gtatatccca    3360
ggtaatacga tagcatgtaa tgattataat aagaatcatg gtgcgaatgc atgtagttct    3420
cgtaatcgtg gatatgacga attctatgga aacaccccag ctgattattc tgcaaatcaa    3480
aaagaatacg ggggtgcgta cacttcccac aatcatgcat atggcgaatc ttatgaaagt    3540
aattcgtcca taccagctga ttatgcgccg gtttatgaag aagaagcgta tacacatgga    3600
cgaagaggta attcttgtga atataacaga gggtatacac cattaccagc tggttatgtg    3660
acagcagagt tagaatactt cccagaaacg gatacagtat gggttgagat tggagaaacg    3720
gaaggaacat ttatcgtgga caatgtggaa ttactcctta tggaggaata g             3771
```

<210> SEQ ID NO 2
<211> LENGTH: 1256
<212> TYPE: PRT
<213> ORGANISM: Bacillus thuringiensis

<400> SEQUENCE: 2

```
Met Thr Ser Asn Arg Lys Asn Glu Asn Glu Ile Ile Asn Ala Leu Ser
1               5                   10                  15

Ile Pro Thr Val Ser Asn Pro Ser Thr Gln Met Asn Leu Ser Pro Asp
                20                  25                  30

Ala Arg Ile Glu Asp Ser Leu Cys Val Ala Glu Val Asn Asn Ile Asp
            35                  40                  45

Pro Phe Val Ser Ala Ser Thr Val Gln Thr Gly Ile Asn Ile Ala Gly
        50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Leu Glu His Val Glu Gln Leu Ile Arg Gln Gln Val
                100                 105                 110

Thr Glu Asn Thr Arg Asn Thr Ala Ile Ala Arg Leu Glu Gly Leu Gly
            115                 120                 125

Arg Gly Tyr Arg Ser Tyr Gln Gln Ala Leu Glu Thr Trp Leu Asp Asn
        130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175
```

-continued

```
Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Thr
        195                 200                 205

Ala Ser Ser Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Val Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285

Arg Glu Val Tyr Thr Asp Ala Ile Gly Thr Val His Pro Ser Gln Ala
    290                 295                 300

Phe Ala Ser Thr Thr Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Tyr Ser Thr Leu Ser Arg Trp Ser Asn Thr Gln Phe
            340                 345                 350

Met Asn Ile Trp Ala Gly His Arg Leu Glu Ser Arg Pro Ile Ala Gly
        355                 360                 365

Ser Leu Asn Thr Ser Thr Gln Gly Ser Thr Asn Thr Ser Ile Asn Pro
    370                 375                 380

Val Thr Leu Gln Phe Thr Ser Arg Asp Ile Tyr Arg Thr Glu Ser Leu
385                 390                 395                 400

Ala Gly Leu Asn Ile Phe Ile Thr Gln Pro Val Asn Gly Val Pro Trp
                405                 410                 415

Val Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Gln Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser His Ile Gly Leu Ile Ser Ser Ser His Val
465                 470                 475                 480

Arg Ala Leu Val Tyr Ser Trp Thr His Arg Ser Ala Asp Arg Thr Asn
                485                 490                 495

Thr Ile Gly Pro Asn Arg Ile Thr Gln Ile Pro Ala Val Lys Gly Arg
            500                 505                 510

Phe Leu Phe Asn Gly Ser Val Ile Ser Gly Pro Gly Phe Thr Gly Gly
        515                 520                 525

Asp Val Val Arg Leu Asn Arg Asn Asn Gly Asn Ile Gln Asn Arg Gly
    530                 535                 540

Tyr Ile Glu Val Pro Ile Gln Phe Thr Ser Thr Ser Arg Tyr Arg
545                 550                 555                 560

Val Arg Val Arg Tyr Ala Ser Val Thr Ser Ile Glu Leu Asn Val Asn
                565                 570                 575

Trp Gly Asn Ser Ser Ile Phe Thr Asn Thr Leu Pro Ala Thr Ala Ala
            580                 585                 590

Ser Leu Asp Asn Leu Gln Ser Gly Asp Phe Gly Tyr Val Glu Ile Asn
        595                 600                 605
```

-continued

Asn Ala Phe Thr Ser Ala Thr Gly Asn Ile Val Gly Val Arg Asn Phe
610                 615                 620

Ser Ala Asn Ala Glu Val Ile Ile Asp Arg Phe Glu Phe Ile Pro Val
625                 630                 635                 640

Thr Ala Thr Phe Glu Ala Lys Tyr Asp Leu Glu Arg Ala Gln Lys Ala
                645                 650                 655

Val Asn Ala Leu Phe Thr Ser Thr Asn Pro Arg Arg Leu Lys Thr Asp
                660                 665                 670

Val Thr Asp Tyr His Ile Asp Gln Val Ser Asn Leu Val Cys Leu
            675                 680                 685

Ser Asp Glu Phe Cys Leu Asp Glu Lys Arg Glu Leu Phe Glu Lys Val
690                 695                 700

Lys Tyr Ala Lys Arg Leu Ser Asp Glu Arg Asn Leu Leu Gln Asp Pro
705                 710                 715                 720

Asn Phe Thr Phe Ile Asn Gly Gln Pro Ser Phe Ala Ser Ile Asp Gly
                725                 730                 735

Gln Ser Asn Phe Thr Ser Ile Asn Glu Leu Ser Asn His Gly Trp Trp
                740                 745                 750

Gly Ser Ala Asn Val Thr Ile Gln Glu Gly Asn Asp Val Phe Lys Glu
            755                 760                 765

Asn Tyr Val Thr Leu Pro Gly Thr Phe Asn Glu Cys Tyr Pro Asn Tyr
770                 775                 780

Leu Tyr Gln Lys Ile Gly Glu Ser Glu Leu Lys Ala Tyr Thr Arg Tyr
785                 790                 795                 800

Gln Leu Arg Gly Tyr Ile Glu Asp Ser Gln Asp Leu Glu Ile Tyr Leu
                805                 810                 815

Ile Arg Tyr Asn Ala Lys His Glu Thr Leu Asn Val Pro Gly Thr Glu
                820                 825                 830

Ser Leu Trp Pro Leu Ser Val Glu Ser Pro Ile Gly Arg Cys Gly Glu
            835                 840                 845

Pro Asn Arg Cys Ala Pro His Phe Gly Trp Asn Pro Asp Leu Asp Cys
850                 855                 860

Ser Cys Arg Asp Arg Glu Lys Cys Ala His His Ser His His Phe Thr
865                 870                 875                 880

Leu Asp Ile Asp Val Gly Cys Thr Asp Leu Gln Glu Asp Leu Gly Val
                885                 890                 895

Trp Val Val Phe Lys Ile Lys Thr Gln Glu Gly Tyr Ala Arg Leu Gly
                900                 905                 910

Asn Leu Glu Phe Ile Glu Glu Lys Pro Leu Ile Gly Glu Ala Leu Ser
            915                 920                 925

Arg Val Lys Arg Ala Glu Lys Lys Trp Arg Asp Lys Arg Glu Lys Leu
930                 935                 940

Gln Val Glu Thr Lys Arg Val Tyr Ile Asp Ala Lys Glu Ala Val Asp
945                 950                 955                 960

Ala Leu Phe Val Asp Ser Gln Tyr Asp Arg Leu Gln Ala Asp Thr Asn
                965                 970                 975

Ile Gly Met Ile His Ala Ala Asp Arg Leu Val His Arg Ile His Glu
            980                 985                 990

Ala Tyr Leu Pro Glu Leu Pro Phe Ile Pro Gly Ile Asn Val Val Ile
            995                 1000                1005

Phe Glu Glu Leu Glu Asn Arg Ile Ser Thr Ala Phe Ser Leu Tyr
    1010                1015                1020

Asp Ala Arg Asn Val Ile Lys Asn Gly Asp Phe Asn Asn Gly Leu
    1025                1030                1035

| | | | | | | | | | | | |
|---|---|---|---|---|---|---|---|---|---|---|---|
| Thr | Cys | Trp | Asn | Val | Lys | Gly | His | Val | Glu | Val | Gln | Gln | Leu | Asn |
| 1040 | | | | 1045 | | | | | 1050 | | |

Thr Cys Trp Asn Val Lys Gly His Val Glu Val Gln Gln Leu Asn
        1040                1045                  1050

Asn His Arg Ser Val Leu Val Ile Pro Glu Trp Glu Ala Glu Val
        1055                1060                  1065

Ser Gln Lys Val Arg Val Cys Pro Gly Arg Gly Tyr Ile Leu Arg
        1070                1075                  1080

Val Thr Ala Tyr Lys Glu Gly Tyr Gly Glu Gly Cys Val Thr Ile
        1085                1090                  1095

His Glu Val Asp Asn Asn Thr Asp Gln Leu Lys Phe Ser Asn Cys
        1100                1105                  1110

Glu Lys Gly Gln Val Tyr Pro Gly Asn Thr Ile Ala Cys Asn Asp
        1115                1120                  1125

Tyr Asn Lys Asn His Gly Ala Asn Ala Cys Ser Ser Arg Asn Arg
        1130                1135                  1140

Gly Tyr Asp Glu Phe Tyr Gly Asn Thr Pro Ala Asp Tyr Ser Ala
        1145                1150                  1155

Asn Gln Lys Glu Tyr Gly Gly Ala Tyr Thr Ser His Asn His Ala
        1160                1165                  1170

Tyr Gly Glu Ser Tyr Glu Ser Asn Ser Ser Ile Pro Ala Asp Tyr
        1175                1180                  1185

Ala Pro Val Tyr Glu Glu Glu Ala Tyr Thr His Gly Arg Arg Gly
        1190                1195                  1200

Asn Ser Cys Glu Tyr Asn Arg Gly Tyr Thr Pro Leu Pro Ala Gly
        1205                1210                  1215

Tyr Val Thr Ala Glu Leu Glu Tyr Phe Pro Glu Thr Asp Thr Val
        1220                1225                  1230

Trp Val Glu Ile Gly Glu Thr Glu Gly Thr Phe Ile Val Asp Asn
        1235                1240                  1245

Val Glu Leu Leu Leu Met Glu Glu
        1250                1255

<210> SEQ ID NO 3
<211> LENGTH: 3771
<212> TYPE: DNA
<213> ORGANISM: Artificial Sequence
<220> FEATURE:
<223> OTHER INFORMATION: Synthetic molecule

<400> SEQUENCE: 3
atgacctcca accgtaagaa cgaaaacgaa atcatcaatg ccctcagcat acccaccgtt      60
agcaatccct ccactcagat gaacctcagc ccagatgcca gaattgagga ctccctctgc    120
gtggcagagg tgaacaacat tgacccttt gtctcagcct ccactgttca aactggcatc    180
aacattgctg ggaggattct tggtgtcctc ggtgtcccat cgctggcca gctcgcttct    240 ttctactcct ttctggttgg tgagctgtgc ccttccggac gtgacccttg gaaatcttc    300 cttgagcacg ttgaacagct gattaggcag caagttactg aaaacacacg taacacagcc    360
attgccagac tggagggtct cggcagagga tatcgcagct atcagcaagc actggaaacg    420
tggctggata acagaaatga tgcaaggtca cgctccatca ttctcgaacg ctacgtggca    480
ctggaacttg acataacaac agccatacct ctgttcagaa tcagaaacca agaagtccct    540
ctgttgatgg tctatgctca agcagccaac ttgcacttgc ttcttttgag ggatgcctct    600
ctgttcggga gcgaatgggg aaccgcttcc agcgacgtga atcagtacta tcaagagcag    660
ataagataca cggaagagta ctcaaatcac tgcgttcagt ggtacaatac tggcttgaac    720
aatctgcgtg gcaccaatgc cgaatcttgg gtgcgttaca tcagttcag aagagacctc    780

```
acacttgggg tgctcgacct cgttgctctc tttccaagct atgacacaag gacttatccc   840
atcaatactt cagcacagct gacgagggaa gtgtacacag acgcaatagg cacagttcac   900
ccctcccaag cctttgcctc cacgacatgg ttcaacaaca atgcaccctc attctcagcc   960
atagaagcag ctgtgattcg tccacccat ttgctggact ttccagagca gttgacgatc   1020
tatagcaccc tttcaaggtg gtcaaacacg caattcatga acatttgggc tggtcataga   1080
cttgagtcaa ggccaatcgc tggttctctt aacacatcaa cccaaggctc caccaacacc   1140
tccatcaacc cagtcaccct ccagttcacc agcagagaca tctatcgcac agaatccctt   1200
gctggactca acatcttcat tacacagcca gtcaatggag tcccgtgggt gaggttcaac   1260
tggaggaatc ccttgaactc acttagggga agccttcttt acaccatagg ttacacgggt   1320
gtgggaacgc agttgcaaga ttcagagact gaactgcctc ccgagaccac cgaacgtccc   1380
aactatgaat catactccca ccgtctgtcc cacattggtc ttatcagctc cagccacgtg   1440
cgtgccctcg tctactcttg gacgcatcgc tccgctgata ggaccaatac cataggtccg   1500
aatagaatca cccagatccc agcagtgaag ggcagattct tgttcaatgg ctctgtcatt   1560
tctggtcctg gtttcactgg tggtgacgtc gttcgcttga acagaaacaa tgggaacatt   1620
caaaaccgtg gttacatcga ggtgcccatc cagtttactt ctacatcaac acgttacaga   1680
gttcgcgtca gatacgcctc tgtgacttct attgaattga acgtgaactg gggaaacagc   1740
tctatcttca ctaacacact tccagccacc gcagcttcac tggacaatct tcagtctggg   1800
gactttggtt atgtggagat caacaatgct ttcacgtctg ccactgggaa cattgttggt   1860
gtgagaaact tctctgccaa tgccgaggtg atcatagata gatttgagtt cattccagtt   1920
actgccacct ttgaggcaaa gtacgatctt gagagagcac agaaggctgt caacgctctg   1980
ttcacaagca ccaacccaag acgtctgaaa actgatgtga cagactatca catcgatcaa   2040
gttagcaact tggtggtttg cctctcagat gagttctgct tggatgagaa gagggaactc   2100
tttgagaagg ttaagtatgc aaaacgcctt tcagacgaaa gaaacttgct gcaagacccc   2160
aactttacgt tcatcaatgg acaacctagc ttcgcttcca ttgatggtca aagcaacttt   2220
acttctatca atgagttgtc taatcacggc tggtgggaa gcgcaaatgt cacaattcaa   2280
gaaggcaacg atgtgttcaa agagaactac gtgacgctgc ctggaacatt caatgagtgt   2340
tatccgaact acttgtatca gaagattggt gaatcagagc tgaaggctta cactcgctat   2400
cagctgcgtg gttacatcga ggactcccaa gaccttgaaa tctatctcat ccgctacaac   2460
gctaaacacg agacattgaa tgttcctgga acagagtccc tttggcctct gtcagttgag   2520
tctcctatag ggaggtgtgg cgaacctaac agatgtgctc ctcactttgg gtggaatccc   2580
gatttggatt gctcttgtag ggatcgcgag aagtgcgctc accattcaca ccactttacg   2640
ctggacatag atgttggctg cacggacctt caagaggatc tcggtgtgtg ggtcgtgttc   2700
aagatcaaaa ctcaagaggg ctacgcaaga ctcgggaatc ttgagttcat tgaggagaag   2760
cctctcattg gcgaggctct ctctagggtg aagagagccg agaagaagtg gcgtgacaag   2820
agggagaaac ttcaagttga gacgaagagg gtgtacattg atgctaaaga ggctgttgat   2880
gcactgtttg tggattcaca gtatgatagg ctccaagctg cacaaaacat tggaatgatt   2940
catgcagcag atcgcctcgt gcatcgcatc catgaggctt atcttccgga actcccgttc   3000
atccctggga tcaatgttgt catctttgag gagcttgaga accgcatatc cacagccttt   3060
tccctctacg atgctagaaa tgttatcaag aatggcgatt tcaacaatgg cttgacgtgt   3120
tggaatgtca aagggcatgt tgaggtccaa cagttgaaca accataggtc agtcctcgtc   3180
```

-continued

```
attccggagt gggaggcaga ggttagccaa aaggtgagag tttgccctgg acgtggctac   3240
attctgagag tcactgccta caaggagggc tacggagaag ggtgcgtcac catccatgaa   3300
gttgataaca atactgacca gttgaagttt tccaactgcg agaaagggca agtgtatcct   3360
gggaatacca ttgcatgtaa cgattacaac aagaatcacg gtgctaacgc ttgctcatct   3420
cgcaataggg gatatgatga gttctatggc aatactccag ctgactactc tgcaaaccag   3480
aaagagtatg gaggagctta caccagccac aaccatgcct atggggaatc ttacgaatcc   3540
aacagcagca tcccagcaga ctatgctccg gtctacgagg aggaagccta cacacatgga   3600
aggaggggaa actcatgtga gtacaataga ggctacactc cgttgccagc tggctacgtc   3660
actgccgaat tggagtactt tccggaaacc gacactgtct gggttgagat aggcgaaact   3720
gagggcacct tcatcgttga caacgtggaa cttctgctta tggaagaata g            3771
```

<210> SEQ ID NO 4
<211> LENGTH: 545
<212> TYPE: PRT
<213> ORGANISM: Bacillus thuringiensis

<400> SEQUENCE: 4

```
Leu Glu Ala Glu Ser Asp Leu Glu Arg Ala Gln Lys Ala Val Asn Ala
1               5                   10                  15

Leu Phe Thr Ser Ser Asn Gln Ile Gly Leu Lys Thr Asp Val Thr Asp
            20                  25                  30

Tyr His Ile Asp Arg Val Ser Asn Leu Val Glu Cys Leu Ser Asp Glu
        35                  40                  45

Phe Cys Leu Asp Glu Lys Lys Glu Leu Ser Glu Lys Val Lys His Ala
    50                  55                  60

Lys Arg Leu Ser Asp Glu Arg Asn Leu Leu Gln Asp Pro Asn Phe Arg
65                  70                  75                  80

Gly Ile Asn Arg Gln Leu Asp Arg Gly Trp Arg Gly Ser Thr Asp Ile
                85                  90                  95

Thr Ile Gln Gly Gly Asp Asp Val Phe Lys Glu Asn Tyr Val Thr Leu
            100                 105                 110

Leu Gly Thr Phe Asp Glu Cys Tyr Pro Thr Tyr Leu Tyr Gln Lys Ile
        115                 120                 125

Asp Glu Ser Lys Leu Lys Ala Tyr Thr Arg Tyr Gln Leu Arg Gly Tyr
    130                 135                 140

Ile Glu Asp Ser Gln Asp Leu Glu Ile Tyr Leu Ile Arg Tyr Asn Ala
145                 150                 155                 160

Lys His Glu Thr Val Asn Val Pro Gly Thr Gly Ser Leu Trp Pro Leu
                165                 170                 175

Ser Ala Pro Ser Pro Ile Gly Lys Cys Ala His His Ser His His Phe
            180                 185                 190

Ser Leu Asp Ile Asp Val Gly Cys Thr Asp Leu Asn Glu Asp Leu Gly
        195                 200                 205

Val Trp Val Ile Phe Lys Ile Lys Thr Gln Asp Gly His Ala Arg Leu
    210                 215                 220

Gly Asn Leu Glu Phe Leu Glu Glu Lys Pro Leu Val Gly Glu Ala Leu
225                 230                 235                 240

Ala Arg Val Lys Arg Ala Glu Lys Lys Trp Arg Asp Lys Arg Glu Lys
                245                 250                 255

Leu Glu Trp Glu Thr Asn Ile Val Tyr Lys Glu Ala Lys Glu Ser Val
            260                 265                 270
```

```
Asp Ala Leu Phe Val Asn Ser Gln Tyr Asp Arg Leu Gln Ala Asp Thr
            275                 280                 285

Asn Ile Ala Met Ile His Ala Ala Asp Lys Arg Val His Ser Ile Arg
        290                 295                 300

Glu Ala Tyr Leu Pro Glu Leu Ser Val Ile Pro Gly Val Asn Ala Ala
305                 310                 315                 320

Ile Phe Glu Glu Leu Glu Gly Arg Ile Phe Thr Ala Phe Ser Leu Tyr
                325                 330                 335

Asp Ala Arg Asn Val Ile Lys Asn Gly Asp Phe Asn Asn Gly Leu Ser
            340                 345                 350

Cys Trp Asn Val Lys Gly His Val Asp Val Glu Glu Asn Asn His
        355                 360                 365

Arg Ser Val Leu Val Val Pro Glu Trp Glu Ala Glu Val Ser Gln Glu
    370                 375                 380

Val Arg Val Cys Pro Gly Arg Gly Tyr Ile Leu Arg Val Thr Ala Tyr
385                 390                 395                 400

Lys Glu Gly Tyr Gly Glu Gly Cys Val Thr Ile His Glu Ile Glu Asn
                405                 410                 415

Asn Thr Asp Glu Leu Lys Phe Ser Asn Cys Val Glu Glu Glu Val Tyr
            420                 425                 430

Pro Asn Asn Thr Val Thr Cys Asn Asp Tyr Thr Ala Thr Gln Glu Glu
        435                 440                 445

Tyr Glu Gly Thr Tyr Thr Ser Arg Asn Arg Gly Tyr Asp Gly Ala Tyr
    450                 455                 460

Glu Ser Asn Ser Ser Val Pro Ala Asp Tyr Ala Ser Ala Tyr Glu Glu
465                 470                 475                 480

Lys Ala Tyr Thr Asp Gly Arg Arg Asp Asn Pro Cys Glu Ser Asn Arg
                485                 490                 495

Gly Tyr Gly Asp Tyr Thr Pro Leu Pro Ala Gly Tyr Val Thr Lys Glu
            500                 505                 510

Leu Glu Tyr Phe Pro Glu Thr Asp Lys Val Trp Ile Glu Ile Gly Glu
        515                 520                 525

Thr Glu Gly Thr Phe Ile Val Asp Ser Val Glu Leu Leu Leu Met Glu
    530                 535                 540

Glu
545

<210> SEQ ID NO 5
<211> LENGTH: 1188
<212> TYPE: PRT
<213> ORGANISM: Artificial Sequence
<220> FEATURE:
<223> OTHER INFORMATION: Chimeric protein; DIG3 core toxin with
      Cry1Ab protoxin

<400> SEQUENCE: 5

Met Thr Ser Asn Arg Lys Asn Glu Asn Glu Ile Ile Asn Ala Leu Ser
1               5                   10                  15

Ile Pro Thr Val Ser Asn Pro Ser Thr Gln Met Asn Leu Ser Pro Asp
            20                  25                  30

Ala Arg Ile Glu Asp Ser Leu Cys Val Ala Glu Val Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80
```

```
Phe Tyr Ser Phe Leu Val Gly Glu Leu Trp Pro Ser Gly Arg Asp Pro
                 85                  90                  95

Trp Glu Ile Phe Leu Glu His Val Glu Gln Leu Ile Arg Gln Gln Val
            100                 105                 110

Thr Glu Asn Thr Arg Asn Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Thr
        195                 200                 205

Ala Ser Ser Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Val Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285

Arg Glu Val Tyr Thr Asp Ala Ile Gly Thr Val His Pro Ser Gln Ala
    290                 295                 300

Phe Ala Ser Thr Thr Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Tyr Ser Thr Leu Ser Arg Trp Ser Asn Thr Gln Phe
            340                 345                 350

Met Asn Ile Trp Ala Gly His Arg Leu Glu Ser Arg Pro Ile Ala Gly
        355                 360                 365

Ser Leu Asn Thr Ser Thr Gln Gly Ser Thr Asn Thr Ser Ile Asn Pro
    370                 375                 380

Val Thr Leu Gln Phe Thr Ser Arg Asp Ile Tyr Arg Thr Glu Ser Leu
385                 390                 395                 400

Ala Gly Leu Asn Ile Phe Ile Thr Gln Pro Val Asn Gly Val Pro Trp
                405                 410                 415

Val Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Gln Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser His Ile Gly Leu Ile Ser Ser Ser His Val
465                 470                 475                 480

Arg Ala Leu Val Tyr Ser Trp Thr His Arg Ser Ala Asp Arg Thr Asn
                485                 490                 495

Thr Ile Gly Pro Asn Arg Ile Thr Gln Ile Pro Ala Val Lys Gly Arg
            500                 505                 510
```

```
Phe Leu Phe Asn Gly Ser Val Ile Ser Gly Pro Gly Phe Thr Gly Gly
        515                 520                 525

Asp Val Val Arg Leu Asn Arg Asn Gly Asn Ile Gln Asn Arg Gly
530                 535                 540

Tyr Ile Glu Val Pro Ile Gln Phe Thr Ser Thr Ser Thr Arg Tyr Arg
545                 550                 555                 560

Val Arg Val Arg Tyr Ala Ser Val Thr Ser Ile Glu Leu Asn Val Asn
                565                 570                 575

Trp Gly Asn Ser Ser Ile Phe Thr Asn Thr Leu Pro Ala Thr Ala Ala
                580                 585                 590

Ser Leu Asp Asn Leu Gln Ser Gly Asp Phe Gly Tyr Val Glu Ile Asn
            595                 600                 605

Asn Ala Phe Thr Ser Ala Thr Gly Asn Ile Val Gly Val Arg Asn Phe
610                 615                 620

Ser Ala Asn Ala Glu Val Ile Ile Asp Arg Phe Glu Phe Ile Pro Val
625                 630                 635                 640

Thr Ala Thr Leu Glu Ala Glu Ser Asp Leu Glu Arg Ala Gln Lys Ala
                645                 650                 655

Val Asn Ala Leu Phe Thr Ser Ser Asn Gln Ile Gly Leu Lys Thr Asp
            660                 665                 670

Val Thr Asp Tyr His Ile Asp Arg Val Ser Asn Leu Val Glu Cys Leu
            675                 680                 685

Ser Asp Glu Phe Cys Leu Asp Glu Lys Lys Glu Leu Ser Glu Lys Val
690                 695                 700

Lys His Ala Lys Arg Leu Ser Asp Glu Arg Asn Leu Leu Gln Asp Pro
705                 710                 715                 720

Asn Phe Arg Gly Ile Asn Arg Gln Leu Asp Arg Gly Trp Arg Gly Ser
                725                 730                 735

Thr Asp Ile Thr Ile Gln Gly Gly Asp Asp Val Phe Lys Glu Asn Tyr
            740                 745                 750

Val Thr Leu Leu Gly Thr Phe Asp Glu Cys Tyr Pro Thr Tyr Leu Tyr
            755                 760                 765

Gln Lys Ile Asp Glu Ser Lys Leu Lys Ala Tyr Thr Arg Tyr Gln Leu
770                 775                 780

Arg Gly Tyr Ile Glu Asp Ser Gln Asp Leu Glu Ile Tyr Leu Ile Arg
785                 790                 795                 800

Tyr Asn Ala Lys His Glu Thr Val Asn Val Pro Gly Thr Gly Ser Leu
                805                 810                 815

Trp Pro Leu Ser Ala Pro Ser Pro Ile Gly Lys Cys Ala His His Ser
            820                 825                 830

His His Phe Ser Leu Asp Ile Asp Val Gly Cys Thr Asp Leu Asn Glu
            835                 840                 845

Asp Leu Gly Val Trp Val Ile Phe Lys Ile Lys Thr Gln Asp Gly His
850                 855                 860

Ala Arg Leu Gly Asn Leu Glu Phe Leu Glu Glu Lys Pro Leu Val Gly
865                 870                 875                 880

Glu Ala Leu Ala Arg Val Lys Arg Ala Glu Lys Lys Trp Arg Asp Lys
                885                 890                 895

Arg Glu Lys Leu Glu Trp Glu Thr Asn Ile Val Tyr Lys Glu Ala Lys
            900                 905                 910

Glu Ser Val Asp Ala Leu Phe Val Asn Ser Gln Tyr Asp Arg Leu Gln
            915                 920                 925

Ala Asp Thr Asn Ile Ala Met Ile His Ala Ala Asp Lys Arg Val His
930                 935                 940
```

```
Ser Ile Arg Glu Ala Tyr Leu Pro Glu Leu Ser Val Ile Pro Gly Val
945                 950                 955                 960

Asn Ala Ala Ile Phe Glu Glu Leu Glu Gly Arg Ile Phe Thr Ala Phe
            965                 970                 975

Ser Leu Tyr Asp Ala Arg Asn Val Ile Lys Asn Gly Asp Phe Asn Asn
        980                 985                 990

Gly Leu Ser Cys Trp Asn Val Lys Gly His Val Asp Val Glu Glu Gln
    995                 1000                1005

Asn Asn His Arg Ser Val Leu Val Val Pro Glu Trp Glu Ala Glu
1010                1015                1020

Val Ser Gln Glu Val Arg Val Cys Pro Gly Arg Gly Tyr Ile Leu
1025                1030                1035

Arg Val Thr Ala Tyr Lys Glu Gly Tyr Gly Glu Gly Cys Val Thr
1040                1045                1050

Ile His Glu Ile Glu Asn Asn Thr Asp Glu Leu Lys Phe Ser Asn
1055                1060                1065

Cys Val Glu Glu Glu Val Tyr Pro Asn Asn Thr Val Thr Cys Asn
1070                1075                1080

Asp Tyr Thr Ala Thr Gln Glu Glu Tyr Glu Gly Thr Tyr Thr Ser
1085                1090                1095

Arg Asn Arg Gly Tyr Asp Gly Ala Tyr Glu Ser Asn Ser Ser Val
1100                1105                1110

Pro Ala Asp Tyr Ala Ser Ala Tyr Glu Glu Lys Ala Tyr Thr Asp
1115                1120                1125

Gly Arg Arg Asp Asn Pro Cys Glu Ser Asn Arg Gly Tyr Gly Asp
1130                1135                1140

Tyr Thr Pro Leu Pro Ala Gly Tyr Val Thr Lys Glu Leu Glu Tyr
1145                1150                1155

Phe Pro Glu Thr Asp Lys Val Trp Ile Glu Ile Gly Glu Thr Glu
1160                1165                1170

Gly Thr Phe Ile Val Asp Ser Val Glu Leu Leu Leu Met Glu Glu
1175                1180                1185

<210> SEQ ID NO 6
<211> LENGTH: 1635
<212> TYPE: DNA
<213> ORGANISM: Artificial Sequence
<220> FEATURE:
<223> OTHER INFORMATION: Synthetic molecule

<400> SEQUENCE: 6
ctcgaggctg aatctgatct cgaaagggca cagaaagctg taaacgcatt gtttacaagt      60
tctaatcaaa tcggactcaa aaccgatgtt acgactatc acatagatag ggtttctaat      120
cttgtggaat gtctttcaga tgagttttgt ttagatgaga agaaagaact ttcagaaaag      180
gtcaagcacg ccaaaagact gtccgatgaa aggaatctcc ttcaagaccc aaactttcgt      240
ggaatcaata ggcagctcga cagaggttgg agagggagca cagatatcac cattcaagga      300
ggagatgacg ttttcaaaga gaactatgtc accttgttag cacctttga tgagtgctat      360 ccaacttatc tgtatcagaa gattgatgaa tccaagctga aggcttacac aagatatcag      420
ctcagaggat acatcgagga ctcccaagat ttggagatat acttgattcg ttacaatgca      480
aaacatgaga ccgtgaatgt tcctggtact ggaagtctct ggccactgtc tgctccgtca      540
cctattggga aatgtgccca tcactcccac catttctcat ggacataga cgttggctgc      600 acagatttga atgaagattt gggtgtttgg gtcatcttca gatcaaaac tcaagacgga      660
```

| | |
|---|---|
| cacgctcgtt taggaaactt agagtttctt gaagagaagc ccttggttgg ggaggcactt | 720 |
| gccagagtaa agagagctga aaagaagtgg agagataaga gggagaaact tgagtgggag | 780 |
| actaacattg tgtacaagga agccaaagaa agcgtggatg ctcttttcgt gaactctcag | 840 |
| tatgataggt tacaagcaga caccaacata gcaatgatac atgcagctga caaaagagtc | 900 |
| cattctattc gtgaggctta cttgccagaa cttagtgtga ttcccggtgt caacgctgcc | 960 |
| attttcgagg aattggaagg aagaatcttt acggctttca gcctctatga cgctaggaat | 1020 |
| gttatcaaga atggtgattt caacaatggc ctctcatgtt ggaatgtgaa aggtcatgtt | 1080 |
| gatgtagagg agcaaaacaa tcaccgtagc gtgctggttg tcccagaatg ggaagccgaa | 1140 |
| gtaagccaag aagttagagt ttgccctgga agaggctaca ttctgcgtgt caccgcttac | 1200 |
| aaagaaggat atggcgaagg gtgcgtgact attcatgaga ttgagaacaa tactgacgaa | 1260 |
| cttaagtttt caaactgcgt cgaggaggaa gtgtatccta caacacagt gacttgtaat | 1320 |
| gactatacag caacgcaaga ggaatacgag gggacataca ccagtcgtaa tcgtggttat | 1380 |
| gatggtgctt atgaaagcaa ttcatccgtt ccagctgact atgccagtgc ctacgaagag | 1440 |
| aaggcttaca cggatggcag aagagataac ccatgtgagt ccaacagagg ttatggtgat | 1500 |
| tacactcctc ttccagctgg ttacgtgact aaagagttag agtactttcc ggagactgat | 1560 |
| aaggtttgga ttgaaatcgg agagacagaa gggacattca tagtagattc agttgagctt | 1620 |
| cttctcatgg aagaa | 1635 |

<210> SEQ ID NO 7
<211> LENGTH: 1635
<212> TYPE: DNA
<213> ORGANISM: Artificial Sequence
<220> FEATURE:
<223> OTHER INFORMATION: Synthetic molecule

<400> SEQUENCE: 7

| | |
|---|---|
| ctcgaggctg aatcggatct tgaaagggca cagaaggcag tcaacgctct cttcaccagc | 60 |
| tcaaatcaga ttggccttaa gaccgatgtt actgactatc atatcgacag agtttctaac | 120 |
| cttgtcgagt gcctctccga cgagttctgt ctcgacgaaa agaaggaact ctccgagaaa | 180 |
| gtgaagcacg cgaaacgcct ctcggatgaa cggaacttgc tgcaagatcc gaacttcaga | 240 |
| ggcatcaatc gccagttgga tagaggctgg aggggatcaa ccgacataac cattcaaggt | 300 |
| ggggatgatg tgttcaagga aaactacgtg acattgctgg gcaccttcga cgagtgctat | 360 |
| cccacgtatc tctatcagaa gattgacgag tccaagctca agcctacac acgctatcag | 420 |
| ctcagaggct acattgagga ctctcaagac ctcgaaatct acttgatcag atacaacgcc | 480 |
| aagcacgaga cggtgaacgt ccctgggact gggtcactgt ggccactgtc ggcaccctcg | 540 |
| ccaatcggaa agtgcgctca ccacagccac cacttctccc ttgacataga tgttgggtgt | 600 |
| acggacttga atgaggatct gggtgtgtgg gtgatcttta agatcaagac ccaagatggt | 660 |
| catgcgaggc ttggcaacct tgagttcctt gaagagaagc ctttggtcgg agaggcactg | 720 |
| gctcgcgtga agagggctga gaagaaatgg agggacaaga gggagaaact ggagtgggag | 780 |
| accaacatag tgtacaagga ggccaaggag tcagtggacg cactgtttgt caattcccag | 840 |
| tatgataggc tccaagcgga cacgaacatc gccatgatcc atgcagcgga caagagggtt | 900 |
| cactccataa gggaggccta tcttccggag ctgtcagtga ttcctggggt caacgcagcc | 960 |
| atctttgagg aattggaagg gaggatcttc accgctttct ctctgtacga cgctcggaac | 1020 |
| gtcatcaaga atggtgattt caacaatgga ctcagctgct ggaacgtgaa agggcatgtc | 1080 |

```
-continued gatgttgaag aacagaacaa tcaccgcagc gtgctggtgg ttccggagtg ggaagccgag    1140
gtctcacaag aagtcagagt gtgccctggg aggggttaca tcttgcgggt cacagcctac    1200
aaggaaggtt atggcgaagg ctgtgtcacg atccatgaga tcgaaaacaa cacagacgag    1260
ctgaagtttt ccaactgtgt tgaggaggag gtctatccta acaatactgt tacgtgcaac    1320
gactacacag ccactcaaga ggagtacgag ggcacttaca cctctcgcaa cagaggctac    1380
gacggtgcct acgagtcaaa cagctccgtg ccagcggact acgcctcggc ttacgaagag    1440
aaggcgtaca ccgacggtcg gagggataac ccgtgcgaga gcaatagagg ctatggcgac    1500
tacactcctc tcccagctgg ctacgtgacc aaggagttgg agtactttcc ggagacagac    1560
aaagtctgga ttgagattgg agagacagaa ggcacgttca tcgtggactc tgttgaactc    1620
ttgctgatgg aggag                                                    1635
```